(12) United States Patent
Hui et al.

(10) Patent No.: US 11,399,845 B2
(45) Date of Patent: Aug. 2, 2022

(54) VASCULAR CAGES AND METHODS OF MAKING AND USING THE SAME

(71) Applicant: Penumbra, Inc., Alameda, CA (US)

(72) Inventors: Delilah Hui, American Canyon, CA (US); Edsel San Diego, San Jose, CA (US); Ben Tompkins, Danville, CA (US)

(73) Assignee: Penumbra, Inc., Alameda, CA (US)

( * ) Notice: Subject to any disclaimer, the term of this patent is extended or adjusted under 35 U.S.C. 154(b) by 73 days.

(21) Appl. No.: 16/215,507

(22) Filed: Dec. 10, 2018

(65) Prior Publication Data

US 2019/0175184 A1   Jun. 13, 2019

Related U.S. Application Data

(60) Provisional application No. 62/597,867, filed on Dec. 12, 2017.

(51) Int. Cl.
*A61B 17/12* (2006.01)
*A61B 17/00* (2006.01)
*A61B 90/00* (2016.01)

(52) U.S. Cl.
CPC .... *A61B 17/1215* (2013.01); *A61B 17/12113* (2013.01); *A61B 17/12172* (2013.01); *A61B 17/12177* (2013.01); *A61B 2017/00526* (2013.01); *A61B 2017/00867* (2013.01); *A61B 2017/00911* (2013.01); *A61B 2017/00915* (2013.01); *A61B 2017/1205* (2013.01); *A61B 2017/12054* (2013.01); *A61B 2017/12063* (2013.01); *A61B 2017/12068* (2013.01); *A61B 2090/3966* (2016.02)

(58) Field of Classification Search
CPC .......... A61B 17/1215; A61B 17/12172; A61B 17/12177; A61B 17/12113; A61B 2017/00911; A61B 2017/12054; A61B 2090/3966; A61B 2017/12063; A61B 2017/12068; A61B 2017/00915; A61B 2017/1205; A61B 2017/00867; A61B 2017/00526
See application file for complete search history.

(56) References Cited

U.S. PATENT DOCUMENTS

| | | | |
|---|---|---|---|
| 5,122,136 | A | 6/1992 | Guglielmi et al. |
| 5,645,558 | A | 7/1997 | Horton |

(Continued)

FOREIGN PATENT DOCUMENTS

WO   WO-2019118374 A1   6/2019

OTHER PUBLICATIONS

"International Search Report for PCT/US2018/064799 dated Feb. 7, 2019".

(Continued)

*Primary Examiner* — Richard G Louis
(74) *Attorney, Agent, or Firm* — Haley Guiliano LLP

(57) ABSTRACT

A vascular cage comprises a self-expandable frame including a plurality of elongated flexible bands. The frame is configured to transition between a compressed configuration and an expanded configuration. The expanded frame may form a three-dimensional cage configured to surround an interior volume as the frame is deployed. At least some of the plurality of bands may have a substantially rectangular cross-section.

27 Claims, 15 Drawing Sheets

(56) References Cited

U.S. PATENT DOCUMENTS

| | | | |
|---|---|---|---|
| 5,766,219 A | 6/1998 | Horton | |
| 5,911,731 A | 6/1999 | Pham et al. | |
| 5,972,019 A | 10/1999 | Engelson et al. | |
| 6,123,714 A | 9/2000 | Gia et al. | |
| 6,193,708 B1* | 2/2001 | Ken | A61B 17/12022 606/1 |
| 6,322,576 B1 | 11/2001 | Wallace et al. | |
| 6,383,174 B1 | 5/2002 | Eder | |
| 6,635,069 B1 | 10/2003 | Teoh et al. | |
| 7,485,123 B2 | 2/2009 | Porter et al. | |
| 7,695,488 B2 | 4/2010 | Berenstein et al. | |
| 8,333,796 B2 | 12/2012 | Tompkins et al. | |
| 8,382,817 B2 | 2/2013 | Pappas et al. | |
| 9,693,852 B2 | 7/2017 | Lam et al. | |
| 2002/0173819 A1* | 11/2002 | Leeflang | A61B 17/22 606/200 |
| 2003/0045898 A1* | 3/2003 | Harrison | A61F 2/013 606/200 |
| 2004/0093017 A1* | 5/2004 | Chanduszko | A61F 2/01 606/200 |
| 2005/0049670 A1 | 3/2005 | Jones et al. | |
| 2005/0065545 A1* | 3/2005 | Wallace | A61B 17/12022 606/200 |
| 2005/0075663 A1 | 4/2005 | Boyle et al. | |
| 2006/0047299 A1 | 3/2006 | Ferguson | |
| 2007/0239193 A1 | 10/2007 | Simon et al. | |
| 2008/0208244 A1 | 8/2008 | Boylan et al. | |
| 2008/0228215 A1 | 9/2008 | Strauss et al. | |
| 2010/0004726 A1* | 1/2010 | Hancock | A61B 17/1214 623/1.2 |
| 2010/0069948 A1* | 3/2010 | Veznedaroglu | A61B 17/12022 606/194 |
| 2010/0174269 A1* | 7/2010 | Tompkins | A61B 17/1214 604/507 |
| 2010/0179512 A1* | 7/2010 | Chong | A61M 25/0138 604/528 |
| 2011/0152993 A1* | 6/2011 | Marchand | A61B 17/12172 623/1.2 |
| 2011/0160760 A1* | 6/2011 | Ferrera | A61B 17/320725 606/194 |
| 2016/0113786 A1 | 4/2016 | Levy et al. | |

OTHER PUBLICATIONS

U.S. Appl. No. 12/558,466, filed Sep. 11, 2009, Erol Veznedaroglu.

* cited by examiner

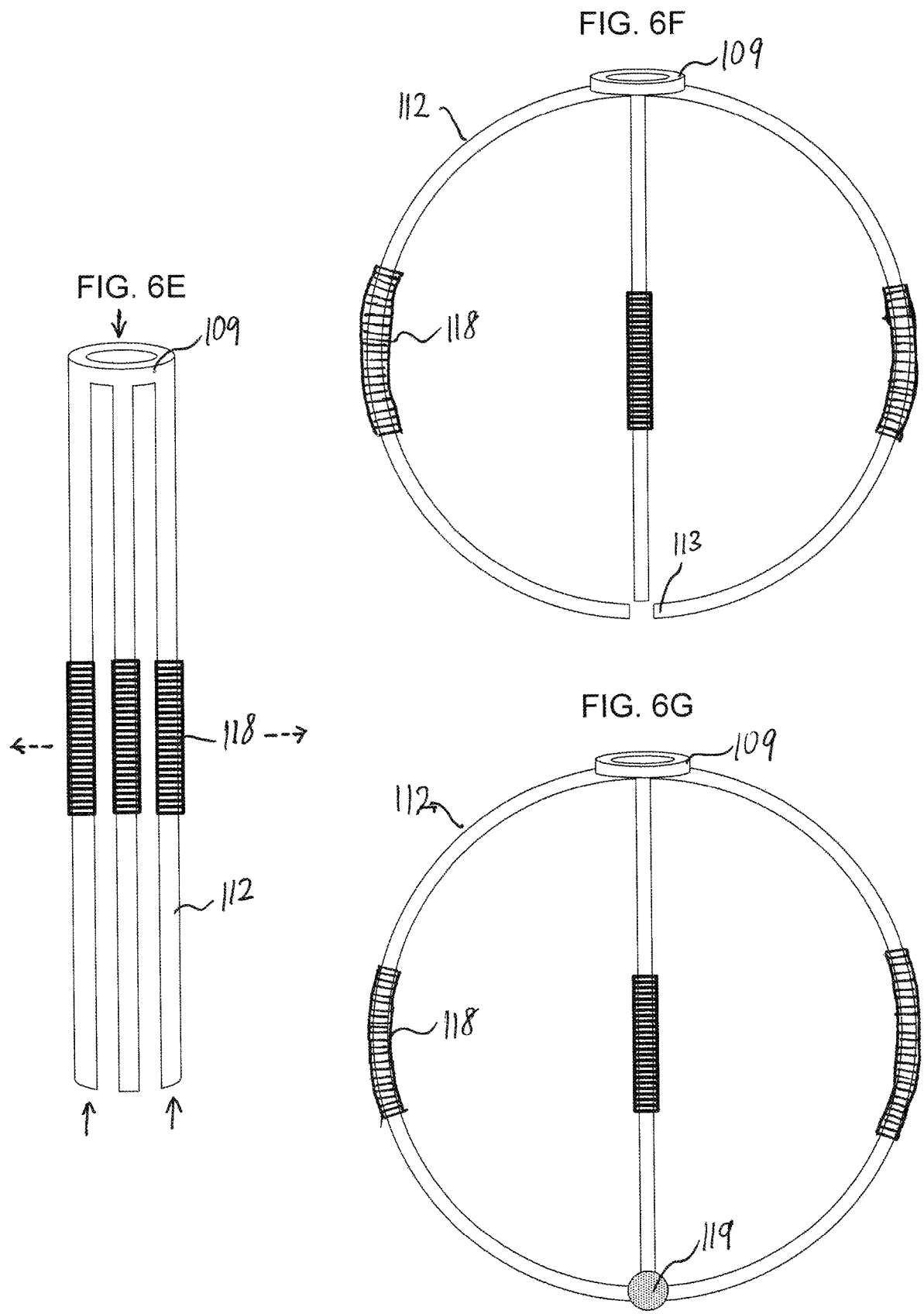

VASCULAR CAGES AND METHODS OF MAKING AND USING THE SAME

CROSS-REFERENCE

This application claims priority to U.S. Provisional Application Ser. No. 62/597,867, filed on Dec. 12, 2017 which is incorporated herein by reference in their entirety.

BACKGROUND OF THE INVENTION

1. Field of the Invention

The present invention relates generally to medical devices and methods. More particularly, the present invention relates to self-expanding vascular cages and other devices which are implantable in aneurysms and other vascular locations.

Vaso-occlusive devices are surgical implants that are placed within an opening in the vasculature which is to be occluded, such as, for example, within an aneurismal cavity to form an embolus by blocking the flow of blood. Vaso occlusive devices may also be used to sacrifice a vessel, for example by deployment within a tumor feeder vessel with the goal of occluding the vessel. Vaso-occlusive devices are typically delivered and placed at a selected site in the vasculature using a catheter in a minimally invasive procedure. In order to create an embolus, numerous coils are implanted in the site, e.g., an aneurysm, until an adequate density has been achieved.

Vaso-occlusive coils are usually constructed of a wire made of a metal or metal alloy wound into a helix. Such vaso-occlusive coils are typically manufactured to assume a certain shape upon discharge of the device from a distal end of a catheter into a treatment site. The shape of the coil is defined by the shape of the coil in a "free energy state," that is a state where there are no outside forces acting on the coil. A variety of such vaso-occlusive coils are known. Such coils may be easily imaged radiographically, readily located at a well-defined vessel site, and retrieved, if necessary. In order for vaso-occlusive coils to be most effective, it is desirable for the coils to fill a peripheral shell of the aneurysm. Ideally, the coils fill the void in a complex, but semi-uniform manner. However, because numerous coils are implanted, it is desirable that the coils do not become overly intertwined or otherwise prevent additional coils from being inserted. It is also desirable to prevent migration of the embolic coils into or within the vessel after the coils have been deployed.

Accordingly, there is a need for a vascular cage that provides a self-expandable frame for framing an interior of an aneurysm, while leaving unobstructed interior space for embolic coils to be deployed thereafter. Additionally, there is a need for a vascular cage that acts as a "backstop" in the vessel for embolic coils deployed within the vessel. Additional needs exist for improving the flexibility of the cage, and the packaging of the compressed cage in its undeployed form in a catheter.

2. Description of the Background Art

The following U.S. Patents and Published Applications describe various self-expanding vaso-occlusive structures, for example, U.S. Patent Application Publication No. 2010/0069948; U.S. Pat. Nos. 8,333,796; 7,485,123; 8,382,817; and 9,693,852.

BRIEF SUMMARY OF THE INVENTION

The inventions described and claimed herein address at least some of the above needs. According to some aspects of the invention, a vascular cage comprises a self-expandable frame including a plurality of elongated flexible bands. The frame is configured to transition between a compressed configuration, usually being externally constrained in a delivery catheter or sheath, and an expanded configuration. The expanded frame may form a three-dimensional cage configured to occupy and/or surround an interior volume within a vascular aneurysm, blood vessel lumen, or the like, as the frame is deployed. At least some of the plurality of bands may have a substantially rectangular cross-section.

In some embodiments, an occlusive system may comprise the aforementioned cage, and a cage delivery catheter or sheath configured to constrain the self-expandable frame in its compressed configuration and to release the self-expandable frame, or "backstop" into a target location in a vasculature in its expanded configuration, e.g. by retracting the catheter or sheath from over the cage and/or by pushing the cage from a distal tip of the catheter or sheath using an internal pusher.

In some instances, each of the plurality of bands may have a substantially rectangular cross-section. Optionally, the substantially rectangular cross-section may be a substantially square cross-section.

The bands may be formed by laser cutting, chemical etching, or otherwise patterning a tube formed from a monolithic block of material having super-elastic and shape memory material properties. In some embodiments, the tube may comprise an elongated nitinol tube. The bands may remain connected at an uncut first end of the tube. Proximal ends of the bands may be cut free from each other and then connected to each other using an attachment material. The proximal ends of the bands may be located at a second end of the tube opposite to the uncut first end of the tube.

As used herein and in the claims, "substantially rectangular cross-section" and "substantially square cross-section" will include annular band cross-sections which result from laser cutting or otherwise patterning tubular structures, as described above, where opposed sides of the annular cross-section may have an arcuate shape and other opposed sides may diverge in a radial direction relative to the tubular structure prior to forming.

In some cases, the distal ends of the bands may remain connected at an uncut second end of the tube located opposite to the uncut first end of the tube. Alternatively, the bands may be fully separated from each other after the tube has been laser cut or otherwise patterned, and the self-expandable frame may be formed by connecting first ends of the bands to each other at a first location and connecting second ends of the bands to each other at a second location.

The substantially rectangular cross-section of at least some of the plurality of bands may allow the bands to be packed more closely in a cage delivery catheter when the self-expandable frame is constrained in its compressed configuration in the catheter. The substantially rectangular cross-section may also allow a higher density of bands to be packed in the catheter with reduced empty space between adjacent bands when the self-expandable frame is constrained in its compressed configuration in the catheter.

In some embodiments, at least one band may comprise a cross-section having varying shape, size, area, and/or longitudinal thickness profile. For example, a band may comprise a first end having a larger cross-sectional area than a second end. Additionally or optionally, a band may comprise a first end having a different cross-sectional shape than a second end. The cross-section having the varying shape, size, area, and/or longitudinal thickness profile may be formed by preferential etching of the band.

The self-expandable frame may be generally spherical or ovoid in its expanded configuration. In some embodiments, the self-expandable frame may comprise at least one dimpled portion in its expanded configuration.

In some embodiments, the cage may further comprise a wire coil wrapped around a portion of at least some of the plurality of bands. The wire coil may comprise a substantially rectangular shaped cross-section. The wire coil may comprise a radio opaque material. The radio opaque material may comprise a metal selected from the group consisting of platinum and platinum alloys. The wire coil may be configured to provide structural reinforcement to said plurality of bands. For example, the wire coil may be wrapped around the portion of the plurality of bands to achieve a predetermined thickness. Additionally or optionally, the wire coil may be wrapped around the portion of the plurality of bands to permit the bands to be packed more closely within a cage delivery catheter when the self-expandable frame is constrained in its compressed configuration in the catheter. The wire coil may also be wrapped around the portion of the plurality of bands to permit a higher density of bands to be packed within the catheter with reduced empty space between adjacent bands when the self-expandable frame is constrained in its compressed configuration in the catheter. The wire coil may be inserted over open ends of the plurality of bands prior to joining the open ends together after the tube has been laser cut. In some cases, the wire coil may not be wrapped around a distal portion of the plurality of bands in order to allow bendability or flexibility of the bands at their distal portions.

In some embodiments, a cage delivery catheter may comprise a shaft having a lumen, a sidewall, at least one urging element formed in the sidewall, and a first filament disposed in the lumen. The self-expandable frame may comprise a second filament having a proximal end including a retention element which is disposed in the lumen of the shaft. The second filament may be fabricated from polymer or metal, and may further have a distal end coupled to a proximal end of the plurality of bands. The retention element may be releaseably retained within the lumen by the first filament which engages the retention element against the urging element in the sidewall to prevent the retention element from exiting a distal end of the shaft. The first filament may be proximally retracted to release the retention member from the urging element and release the plurality of bands from the distal end of the lumen. In some embodiments, the retention element may comprise a ball and the sidewall may comprise an aperture.

In some embodiments, the cage may further comprise a pusher wire having an attachment fixture thereon, and a severable deployment junction located at proximal ends of the plurality of bands releasably connecting each of said plurality of bands to said pusher wire.

In some embodiments, the three-dimensional cage may provide an interior space allowing one or more smaller filling coils to be deployed therein.

In some embodiments, the self-expandable frame may comprise three to ten elongated flexible bands, preferably six to eight elongated flexible bands.

Further aspects of the invention provide a method of forming a vascular cage. The method may comprise providing a tube, and laser cutting the tube to form a plurality of elongated flexible bands. At least some of the plurality of bands may have a substantially rectangular cross-section. The method may further comprise forming a self-expandable frame comprising the plurality of bands. The frame is configured to transition between a compressed configuration and an expanded configuration. The expanded frame may form a three-dimensional cage configured to surround an interior volume as the frame is deployed.

In some embodiments of the aforementioned method, the tube may be fabricated from a monolithic block of material having super-elastic and shape memory material properties. For example, the tube may comprise an elongated nitinol tube. The tube may be laser cut such that the bands remain connected at an uncut first end of the tube. In some cases, proximal ends of the bands may be cut free from each other, and the distal ends of the bands may be located at a second end of the tube opposite to the cut first end of the tube. The self-expandable frame may be formed by connecting the proximal ends of the bands using an attachment material. Alternatively, the tube may be laser cut such that the bands remain connected at an uncut second end of the tube opposite to the first end of the tube. In some further examples, the tube may be laser cut such that the bands are fully separated from each other, and the self-expandable frame may be formed by connecting first ends of the bands to each other at a first location and connecting second ends of the bands to each other at a second location.

In some embodiments, the method may further comprise inserting a wire coil over an open end of at least some of the plurality of bands, and wrapping the wire coil around a portion of the bands. The wire coil may comprise a substantially rectangular shaped cross-section. The wire coil may comprise a radio opaque material. For example, the radio opaque material may comprise a metal selected from the group consisting of platinum and platinum alloys.

Additional aspects of the invention provide a method of occluding a vascular location. The method may comprise providing the vascular cage, delivering the vascular cage while constrained in its compressed configuration to a target site in the vasculature, and releasing the cage from constraint so that it expands to its expanded configuration at the target location. Delivering the vascular cage may comprise positioning a distal end of a cage delivery catheter at a target location in a patient's vasculature, and advancing the cage in its compressed configuration through a lumen of the cage delivery catheter. Releasing the cage from constraint may comprise releasing the cage from the distal end of the cage delivery catheter so that the frame self-expands at the target location. The target location may be an aneurysm. Additionally or optionally, the target location may be a blood vessel lumen. In some embodiments, the method may further comprise delivering coils into the interior volume of the vascular cage after the vascular cage has been released.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 6A-6G illustrate a method of forming a vascular cage comprising a self-expandable frame in accordance with an embodiment;

DETAILED DESCRIPTION OF THE INVENTION

Figure 1A:
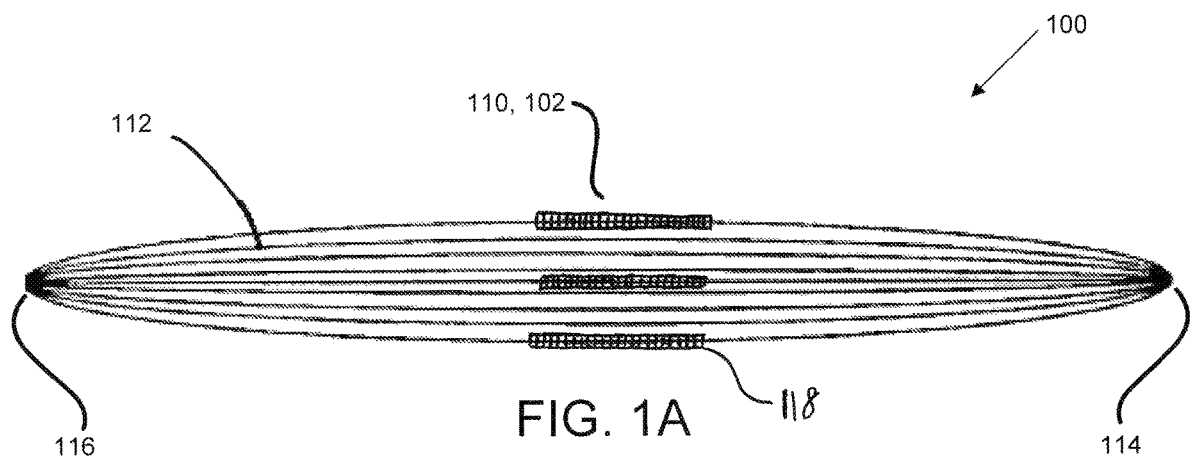
FIG. 1A shows a self-expandable frame in a compressed configuration in accordance with an embodiment.

While preferred embodiments of the present invention have been shown and described herein, it will be appreciated by those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

It should be noted that the accompanying figures are intended to illustrate the general characteristics of methods and materials with reference to certain example embodiments of the invention and thereby supplement the detailed written description provided below. These drawings are not, however, to scale and may not precisely reflect the characteristics of any given embodiment, and should not be interpreted as defining or limiting the range of values or properties of embodiments within the scope of this invention. In particular, the relative sizing and positioning of particular elements and structures may be reduced or exaggerated for clarity. The use of similar or identical reference numbers in the various drawings is intended to indicate the presence of a similar or identical element or feature.

The invention provides a vascular cage comprising a self-expandable frame. The frame may include a plurality of elongated flexible bands. The frame is configured to transition between a compressed configuration, usually being externally constrained in a delivery catheter or sheath, and an expanded configuration. The expanded frame may form a three-dimensional cage configured to occupy and/or surround an interior volume within a vascular aneurysm, blood vessel lumen, or the like, as the frame is deployed. At least some of the plurality of bands may have a substantially rectangular cross-section to improve packing of the bands in a cage delivery catheter.

Additional wire coils may be wrapped around a portion of at least some of the bands for reinforcement of the bands, and increasing overall thickness of the bands. Wires may be wound around a square-shaped mandrel to form coils with substantially rectangular cross sections. The substantially rectangular cross sections of the wrapped bands can reduce overall thickness of the compressed frame by eliminating empty space between adjacent bands, and can allow a higher density of bands to be packed into the catheter.

When the self-expandable frame is deployed in a target location, the expanded frame "frames" the interior of the target location, leaving interior space for filling coils to be deployed thereafter. Alternatively, when the self-expandable frame is deployed in a target location, the frame functions as a "backstop", preventing migration of coils to be deployed thereafter. The frame described herein can frame aneurysms much more expeditiously than conventional "3-dimensional" framing coils. For example, a shorter distance is needed to push the compressed frame out of the catheter to frame an aneurysm, and framing the aneurysm can be completed more quickly using the frame described herein compared to conventional framing coils.

Various aspects of the invention described herein may be applied to any of the particular applications set forth below and for any other types of vaso-occlusive coils, cages, framing coils, etc. The invention may be applied as a standalone apparatus or method, or as part of a medical system. It shall be understood that different aspects of the invention can be appreciated individually, collectively, or in combination with each other.

Figure 1B:
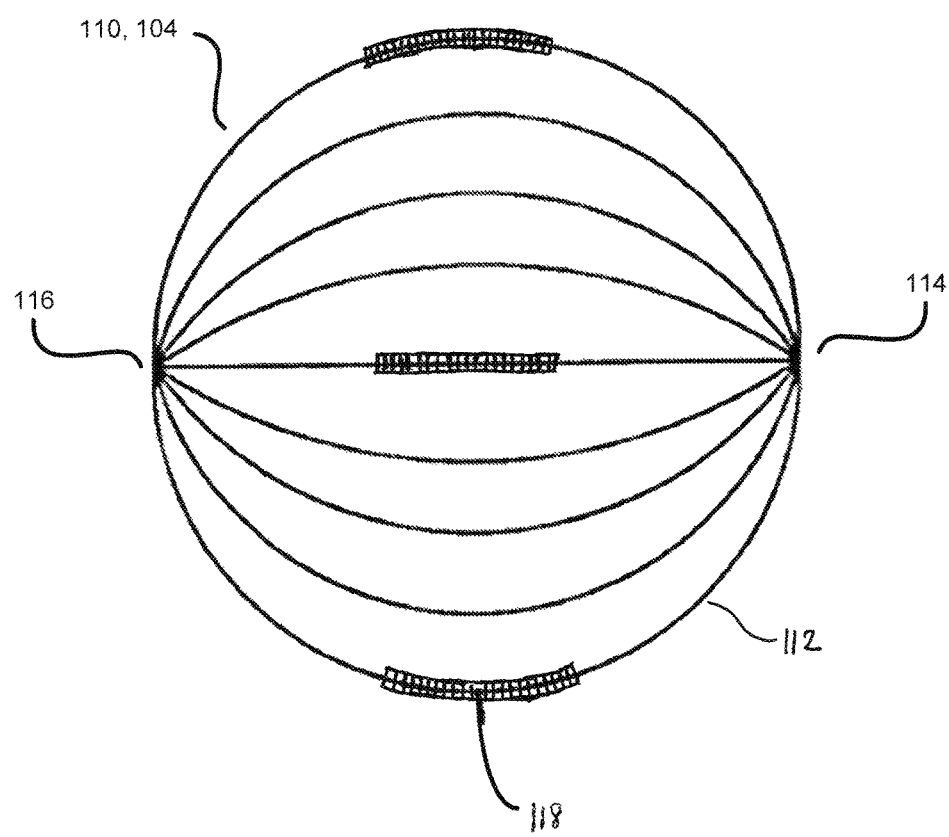
FIG. 1B shows a vascular cage comprising the self-expandable frame of FIG. 1A in an expanded configuration in accordance with an embodiment.

FIGS. 1A and 1B illustrate a vascular cage 100 in accordance with an embodiment. The cage can be used for treatment of an aneurysm. Additionally or optionally, the cage can be used in vascular locations other than aneurysms. The cage may comprise a self-expandable frame 110 including a plurality of elongated flexible bands 112. First ends of the bands are connected to each other at a first location 114, and second ends of the bands are connected to each other at a second location 116. The first and second locations 114/116 may be at opposite ends of the frame.

The plurality of bands 112 may be formed by laser cutting, chemical etching, or otherwise patterning of a tube (not shown). For example, slots can be laser cut along a length of the tube to form bands. The tube may be extruded from a monolithic block of material. The tube may have super-elastic and shape memory material properties. In some embodiments, the tube may be an elongated nitinol tube. At least some of the plurality of bands may have a substantially rectangular cross-section as a result of the laser cutting process. The substantially rectangular cross-section may be, for example a substantially square cross-section. In some embodiments, the tube may be laser cut such that each of the plurality of bands has a substantially rectangular cross-section. In other embodiments, the tube may be laser cut such that a first set of bands have a substantially rectangular cross-section, and a second set of bands have cross-sections that are non-rectangular. Non-limiting examples of non-rectangular cross-sections may include any polygonal shapes such as triangular, pentagonal, hexagonal, etc. In some alternative embodiments, at least some of the plurality of bands may have a substantially circular, oval, or semi-circular cross-section.

In some embodiments, at least one band may comprise a cross-section having varying shape, size, area, and/or longitudinal thickness profile. For example, a band may comprise a first end having a larger cross-sectional area than a second end. In some cases, a band may comprise a first end having a different cross-sectional shape than a second end. Such variations in cross-section of the band can be formed by preferential etching of the band, either alone or in conjunction with laser cutting.

In some embodiments, the plurality of bands may remain connected at an uncut first end of the tube after the tube has been laser cut. Proximal ends of the bands may be cut free from each other and then connected to each other using an attachment material including solders, welds, adhesives, epoxies, glues and the like. The proximal ends of the bands may be located at a second end of the tube opposite to the uncut first end of the tube. In some alternative embodiments, proximal ends of the bands remain connected at an uncut second end of the tube, and the uncut first and second ends of the tube may be located at opposite ends of the tube. In some further embodiments, the bands may be fully separated from each other after the tube has been laser cut, and the self-expandable frame may be formed by connecting first ends of the bands to each other at a first location (e.g. 114) and connecting second ends of the bands to each other at a second location (e.g. 116).

In some embodiments, the cage 100 may further comprise a wire coil 118 wrapped around a portion of at least some of the plurality of bands. The wire coil may be wrapped such that it conforms to the cross-section shape and/or longitudinal profile of the bands. For example, the wire coil may comprise a substantially rectangular shaped cross-section conforming to bands having substantially rectangular cross-sections. The wire coil may aid in radiofluoroscopy imaging and may comprise a radio opaque material. The radio opaque material may include metals such as platinum or platinum alloys. In some embodiments, the wire coil may be preferably constructed of platinum and its alloys in order to take advantage of the properties of these materials with respect to their ability to retain memory for shape, resistance to biological fluids, softness and non-ferromagnetic properties that will allow patients to undergo MIll procedures and pass through metal detectors. Although platinum and its alloys are preferred for the wire coil, those skilled in the art will appreciate that other materials and, in some instances, combinations of two or more materials including, for example, other metals and polymers, may also be utilized for the wire coil.

The wire coil can provide structural reinforcement to the bands. For example, the wire coil can be wrapped around a portion of some of the bands to achieve a predetermined thickness. Wrapping the wire coil around some of the bands can allow the bands to be packed more closely within a cage delivery catheter when the frame is constrained in its compressed configuration in the catheter. For example, a higher density of bands can be packed within the catheter with reduced empty space between adjacent compressed bands.

In some embodiments, the tube may be laser cut such that proximal ends of the bands are cut free from each other. A free end of one or more bands may be inserted into a lumen of one or more wire coils, and then the coil may be moved along the bands to a predefined location, prior to joining the free/open ends of the bands. As previously described, the open ends of the bands can be connected using any attachment material such as solders, welds, adhesives, epoxies, glues and the like.

Although FIGS. 1A and 1B show the wire coils being wrapped around a central portion of some of the bands, the invention is not limited thereto. In some embodiments, a wire coil may be wrapped around each of the plurality of bands. Alternatively, a coil may be wrapped around only a single band. In some embodiments, a wire coil may be wrapped around the bands in an alternating or staggered manner. For example, a wire coil may be wrapped around every other adjacently-spaced band.

In some embodiments, a wire coil may be wrapped covering a substantial length of a band. A wire coil may consist of a single coil extending along the length of the band. Alternatively, a plurality of wire coils may be wrapped along a band and spaced apart from each other. The spacing between adjacent coils along a band can be fixed, uniform, staggered, or random. In some embodiments, a wire coil may be movable after it is wrapped around a band, and can slide to any location along the band. Optionally, a wire coil may be rigidly affixed (immobilized) after it is wrapped around a band. In some embodiments, the wire coil is not wrapped around a distal portion of a band, and may be placed a minimum distance away from the distal end of the band in order to allow the band to sufficiently bend or flex at its distal portion.

The frame 110 is configured to transition between a compressed configuration 102 and an expanded configuration 104. As shown in FIG. 1A, the compressed frame may be generally elongated with the plurality of bands and coils packed closely together in a longitudinal manner. Referring to FIG. 1B, the expanded frame may be generally spherical or ovoid, with the plurality of bands curved outward and spaced apart from each other. In some embodiments, the expanded frame may be a simple closed geodesic, with meridians corresponding to the plurality of bands 112, and opposing poles at locations 114 and 116. The expanded frame can form a three-dimensional cage configured to occupy and/or surround an interior volume within a vascular aneurysm, blood vessel lumen, or the like, as the frame is deployed. For example, the expanded frame can be configured to frame an interior of an aneurysm, thereby providing a cage in the aneurysm. The three-dimensional cage can provide an interior unobstructed space allowing one or more smaller filling coils to be subsequently deployed therein.

The frame can transition between the compressed configuration and the expanded configuration with aid of a cage delivery catheter as described in more detail with reference to FIGS. 2A-C. The frame is configured to naturally expand outward in the absence of an external force or physical constraints applied to the frame. The frame is configured to expand to a predetermined shape, volume, and/or size unless otherwise constrained. Constraints may be imposed on the frame, for example by the catheter or by vasculature. The catheter can be configured to constrain the frame in its compressed configuration, and to release the frame into a target location (e.g., an aneurysm) in the vasculature in its expanded configuration, e.g. by retracting the catheter or sheath from over the cage and/or by pushing the cage from a distal tip of the catheter or sheath using an internal pusher. When the frame is deployed at the target location, the frame will expand until it is constrained by the interior of the target location, or until it reaches its predetermined shape, volume and/or size, depending on which occurs first.

Figure 2A:
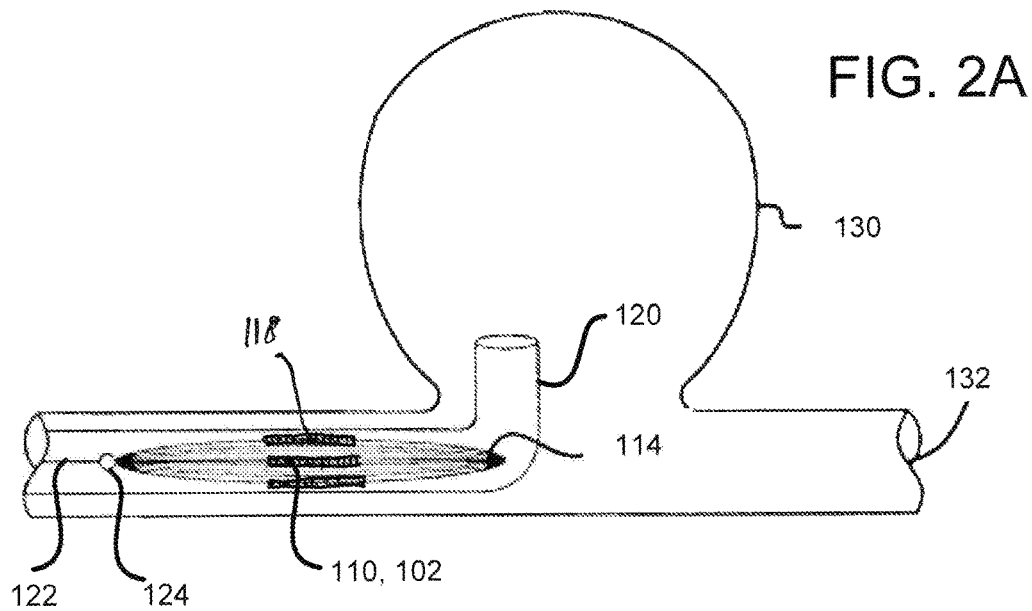
FIG. 2A shows a cage delivery catheter constraining the self-expandable frame in its compressed configuration in accordance with an embodiment.
Figure 2B:
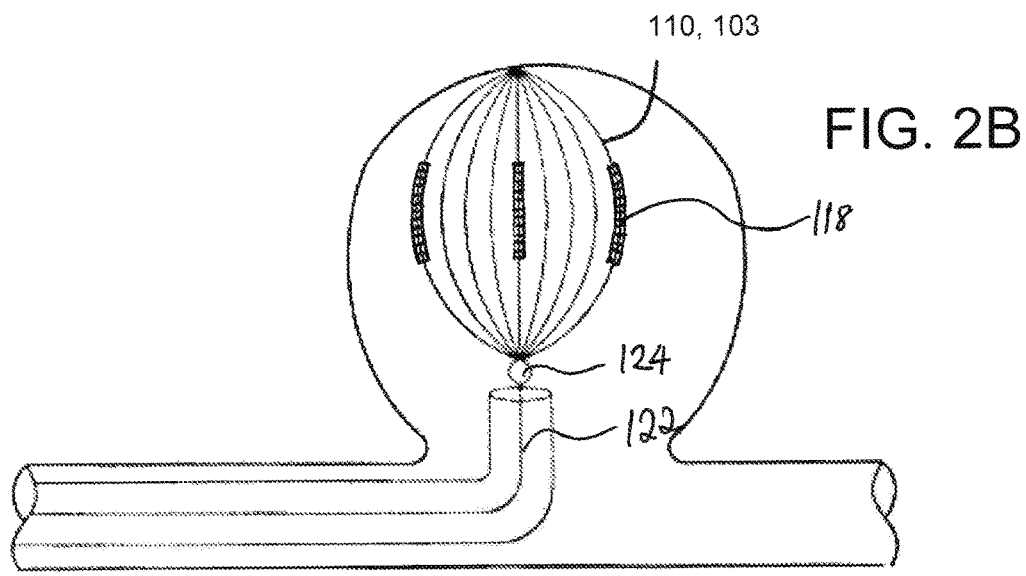
FIG. 2B shows the self-expandable frame in a partially deployed state in a target location.
Figure 2C:
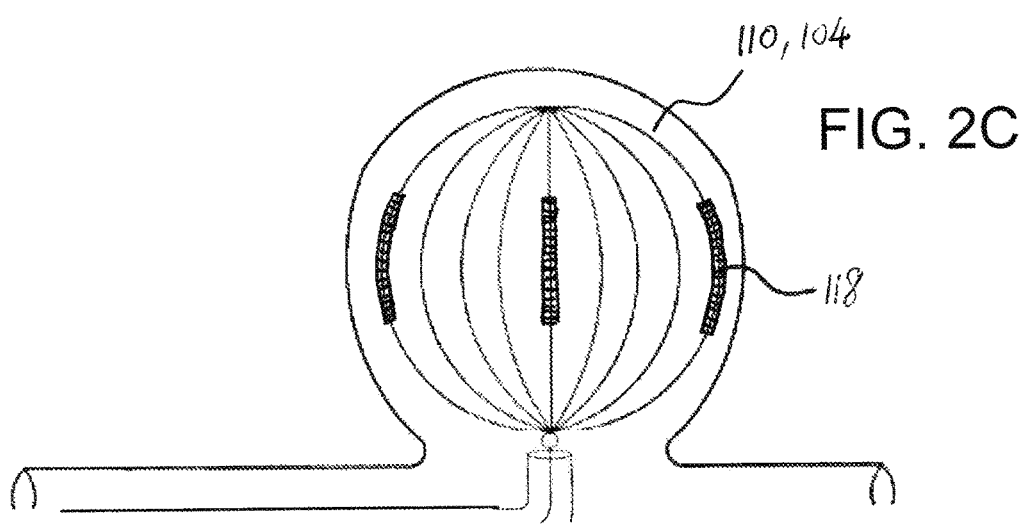
FIG. 2C shows full deployment of the self-expandable frame in the target location accordance with an embodiment.

FIGS. 2A-2C illustrate deployment of a self-expandable frame using a cage delivery catheter 120 in accordance with an embodiment. The catheter can be configured to hold and deliver the self-expandable frame 110 to any target location or site for treatment. For example, the frame can be deployed into an aneurysm 130 extending from a primary or parent blood vessel 132. Referring to FIG. 2A, the frame 110 may be delivered in a collapsed or compressed configuration 102 in an undeployed state through the catheter 120 to the site of the aneurysm 130. In some embodiments, the compressed frame may be pushed through the catheter with a pusher 122 until the frame exits the catheter and deploys into the aneurysm. The pusher may comprise a thin wire (often referred to as a pusher wire) for pushing the compressed frame through the catheter. As the frame exits the catheter, it transitions from the compressed configuration 102 to the expanded configuration 104, and is allowed to expand within the aneurysm to achieve a completely deployed state. FIG. 2B shows the frame in a partially deployed state 103 as it self-expands within the aneurysm, and FIG. 2C shows the expanded frame in its fully deployed state 104 framing the interior of the aneurysm.

In some embodiments, the expanded frame may be separated from the pusher 122 via a deployment junction 124 after the frame has been fully deployed in the aneurysm. The junction 124 may be located at proximal ends of the plurality of bands releasably connecting the frame to the pusher. The expanded frame may be separated from the pusher through electrolytic or thermal means at the deployment junction, as known to those skilled in the art.

After the expanded frame has been separated from the pusher, the catheter and/or pusher may be withdrawn from the parent blood vessel, leaving the expanded frame in the aneurysm. The frame may be appropriately sized for the aneurysm under treatment, such that the size of the fully expanded frame exceeds the opening from the parent vessel into the aneurysm. This allows the expanded frame to be retained indefinitely within the aneurysm and will not present any loose ends that would extend out of the aneurysm.

In one optional embodiment, the frame may be retracted back into the catheter during the deployment process by pulling the pusher back into the catheter thereby causing the frame to follow. During retraction, the frame will transform from its expanded configuration back into a compressed configuration to enter the catheter.

In some further embodiments, the self-expandable frame need not be deployed via a severable junction, and may be mechanically deployed through the catheter in a similar fashion to a stent deployment. A cage delivery catheter may comprise a shaft having a lumen, a sidewall, at least one urging element formed in the sidewall, and a first filament disposed in the lumen. The self-expandable frame may comprise a second filament having a proximal end including a retention element which is disposed in the lumen of the shaft. The second filament may be fabricated from metal or from polymer, and may have a distal end coupled to a proximal end of the plurality of bands. The retention element may be releaseably retained within the lumen by the first filament which engages the retention element against the urging element in the sidewall to prevent the retention element from exiting a distal end of the shaft. The first filament may be proximally retracted to release the retention member from the urging element and release the plurality of bands from the distal end of the lumen. In some embodiments, the retention element may comprise a ball, and the sidewall of the catheter may comprise an aperture.

Referring back to FIG. 2C, the expanded frame can at least partially fill and stabilize the aneurysm under treatment. The frame may be used alone or may be used in combination with other vaso-occlusive devices, including conventional coils, and/or materials that can promote and/or suppress certain effects and responses within the aneurysm and the surrounding tissue. A variety of coatings and compositions have, for example, been proposed for enhancing or accelerating embolization.

Figure 3A:
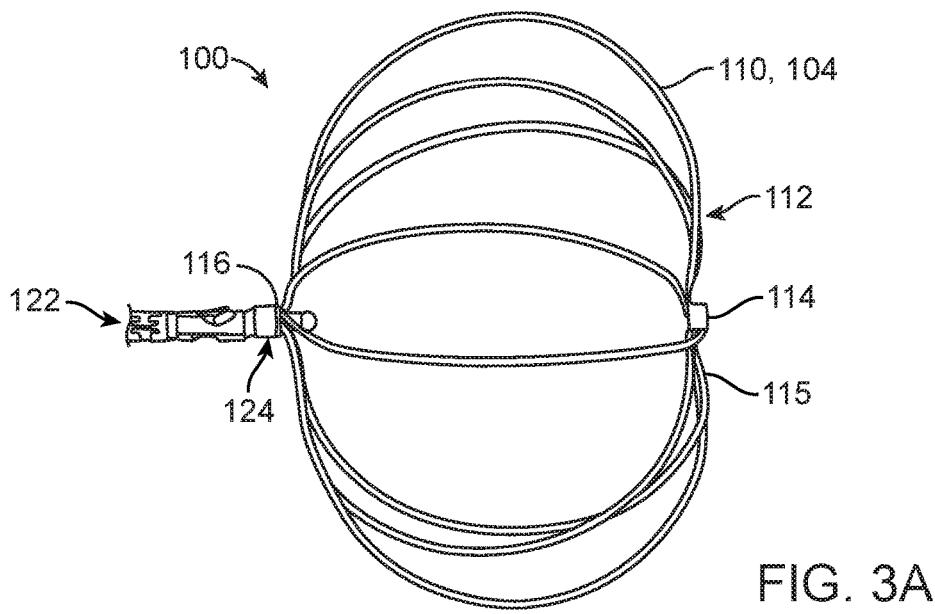
FIG. 3A shows a vascular cage comprising a self-expandable frame in an expanded configuration and coupled to a pusher via a deployment junction, in accordance with an embodiment.
Figure 3B:
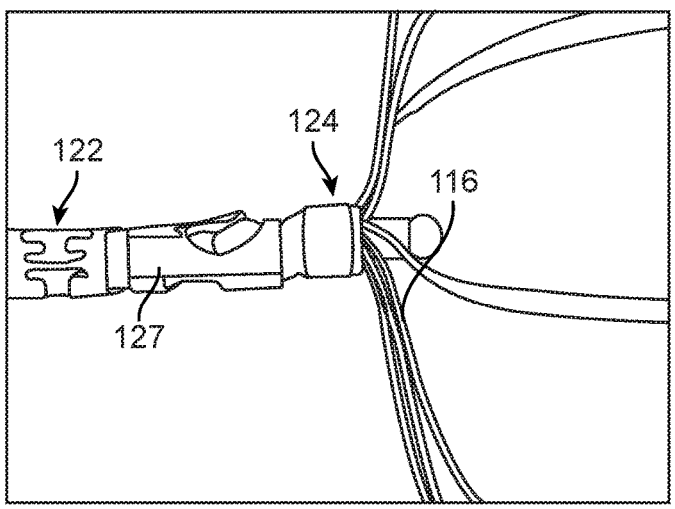
FIG. 3B shows a close-up view of the pusher and deployment junction of FIG. 3A.
Figure 3C:
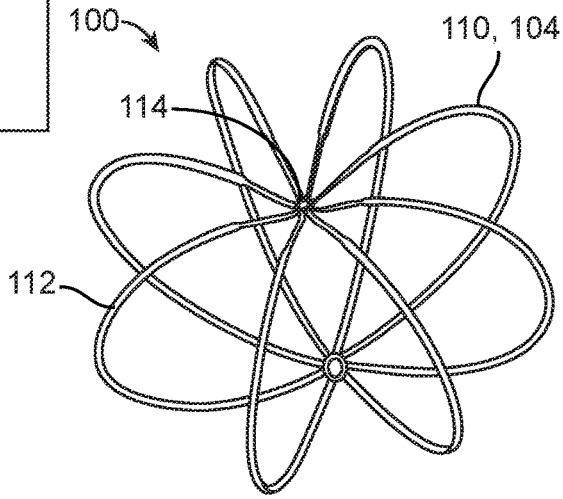
FIG. 3C shows a top perspective view of the expanded frame of FIG. 3A after the frame has been released from the pusher.

FIGS. 3A-3C illustrate a cage in accordance with an embodiment. The cage 100 may comprise a self-expandable frame 110 comprising a plurality of bands 112 as described elsewhere herein. First ends of the bands may be connected to each other at a first location 114, and second ends of the bands may be connected to each other at a second location 116. The first and second locations may be at opposite ends of the frame. FIG. 3A shows a side view of the frame 110 in an expanded configuration 104, and FIG. 3C shows a perspective view of the expanded frame from above. The expanded frame may be generally spherical or ovoid, with the plurality of bands curved outward and spaced apart from each other. Although FIG. 3C shows the frame having eight bands, it should be appreciated that any number of bands may be contemplated. For example, the frame may have between three to ten bands, preferably six to eight bands. In some embodiments, the frame may have more than ten bands.

In some embodiments, the frame may further comprise at least one dimpled portion 115 in its expanded configuration, for example as shown in FIG. 3A. The dimpled portion may correspond to a slightly concaved portion of the frame. The dimpled portion may be near the first location 114 at the distal portion of the expanded frame. The dimpled portion can help to minimize interaction/contact between the distal portion of the expanded frame and the interior of the aneurysm. For example, any sharp or pointed edges at the distal portion of the expanded frame can be recessed into the dimpled portion, thereby preventing those edges from contacting the interior of the aneurysm or penetrating surrounding tissue. The dimpled portion may result in the expanded frame having a compressed spherical shape with a concaved end. The expanded frame can form a three-dimensional cage configured to occupy and/or surround an interior volume within a vascular aneurysm, blood vessel lumen, or the like, as the frame is deployed. For example, the expanded frame can be configured to frame an interior of an aneurysm, thereby providing a cage in the aneurysm.

The cage may further comprise a pusher 122 coupled to the frame 110 via a deployment junction 124. The junction may be located at proximal ends of the plurality of bands, for example near the second location 116 of the frame, mated with the distal end of the pusher 122, as shown in the close-up view in FIG. 3B. The distal end of pusher 122 includes urging element 127. The junction may releasably connect the frame to the pusher. When the compressed frame is in the catheter, the frame may be connected to the pusher at the deployment junction such that the pusher is capable of advancing and delivering the compressed frame through the catheter. When the expanded frame is fully deployed in a target location of the vasculature, the deployment junction can be configured to release the frame from the pusher, and urging element 127 propels the release of the frame. Alternatively, the expanded frame may be separated from the pusher through electrolytic or thermal means at the deployment junction, as known to those skilled in the art. Subsequently, the pusher can be retracted away from the target location with the expanded frame remaining in the target location.

Figure 4A:
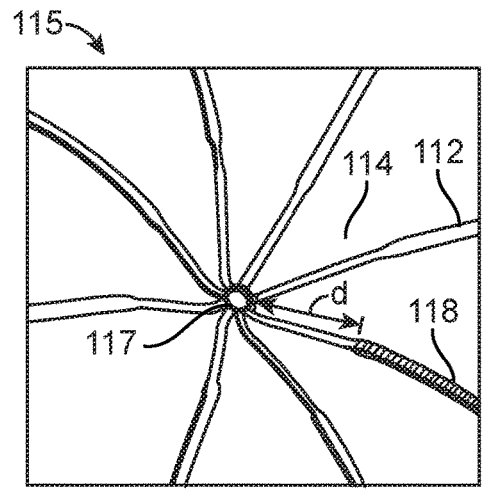
FIG. 4A shows a wire coil wrapped around a portion of some of a plurality of bands in accordance with an embodiment.

FIG. 4A shows a close-up view of the first location 114 and the dimpled portion 115 of the expanded frame. The plurality of bands may be connected to each other at their distal ends via a ring 117. As previously described, the bands may be formed by laser cutting, chemical etching, or otherwise patterning a tube comprising a monolithic block of material. The ring 117 may correspond to an uncut end of the tube. The ring can be configured to support and hold the bands together. The ring can also be configured to withstand multiple expansions and compressions of the frame (multiple flexing and bending of the bands) without the bands yielding or breaking.

Figure 4B:
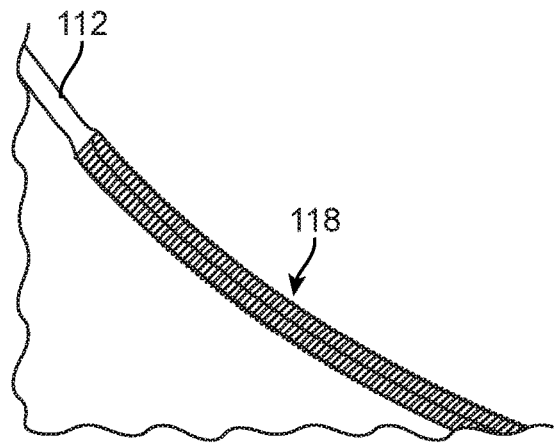
FIG. 4B is a close-up view of FIG. 4A showing a wire coil wrapped around a portion of a band.
Figure 4C:
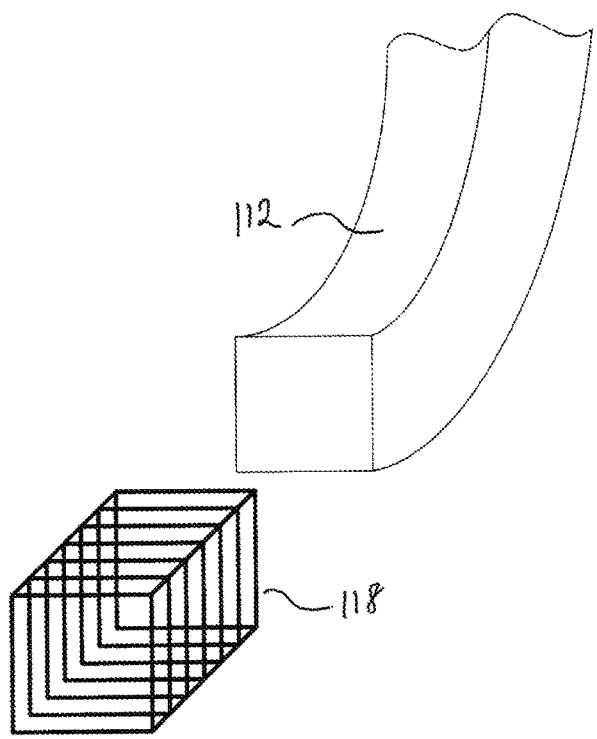
FIG. 4C is a schematic perspective view separately showing a curved band and a wire coil, each having a substantially rectangular cross-section in accordance with an embodiment.
Figure 4D:
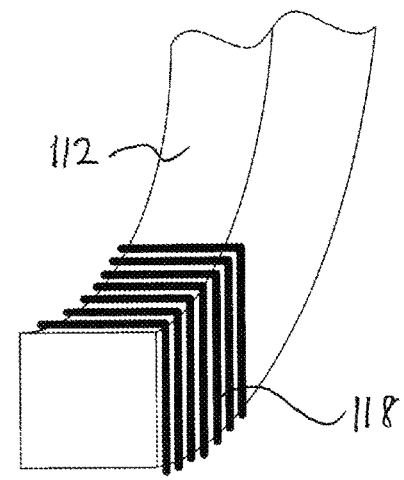
FIG. 4D is a schematic perspective view showing a wire coil wrapped around a portion of a curved band.
Figure 4E:
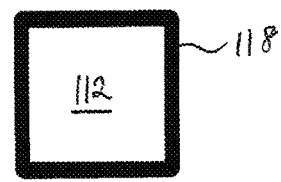
FIG. 4E is a schematic cross-section view of a band wrapped with a wire coil.

FIG. 4A further shows a wire coil 118 wrapped around a portion of at least some of the plurality of bands. FIG. 4B is a close-up view of a wire coil wrapped around a band. FIG. 4C is a schematic perspective view separately showing a curved band and a wire coil, each having a substantially rectangular cross-section. FIG. 4D is a schematic perspective view showing the wire coil wrapped around a portion of the band. FIG. 4E is a schematic cross-section view showing the wire coil wrapped around a portion of the band. As shown in FIGS. 4C-4E, the wire coil may wrap around and conform to the shape of the band such that the wire coil also has a substantially rectangular shaped cross-section. The wire coil may aid in radiofluoroscopy imaging, and may comprise a radio opaque material including metals such as platinum or platinum alloys. The wire coil can also provide structural reinforcement to the band. For example, the wire coil can be wrapped around a portion of the band to achieve any predetermined thickness. In some embodiments, multiple rounds of the wire coil can be wrapped around the band to increase its thickness and structural rigidity. Accordingly, the rigidity or flexibility of a band can be customized based on the material type, thickness, location, and number of windings of the wire coil around the band. Referring to FIG. 4A, the wire coil may not be wrapped around a distal portion of the band in some embodiments. For example, the wire coil may be placed a minimum distance d away from the distal end of the band in order to allow the band to sufficiently bend or flex at its distal portion. The distance d may be measured from the ring 117 to the near edge of the wire coil.

As previously described, the wire coil may be wrapped around a selected number of bands. In some embodiments, the wire coil may be wrapped around all of the bands. Alternatively, the wire coil may be only wrapped around a single band. The wire coil may be wrapped continuously along a portion of a band. Alternatively, multiple wire coils may be wrapped continuously along a band and spaced apart from each other.

Figure 5A:
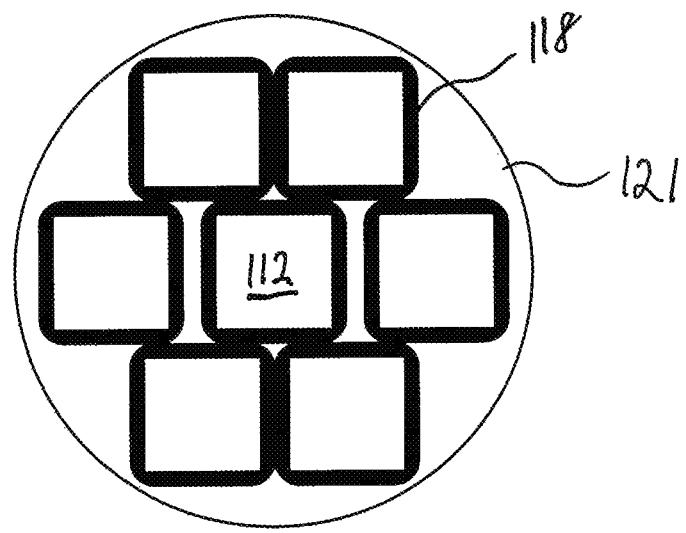
FIG. 5A is a schematic cross-section view showing the packing of bands in a catheter comprising a shaft having a circular-shaped lumen, in accordance with an embodiment.
Figure 5B:
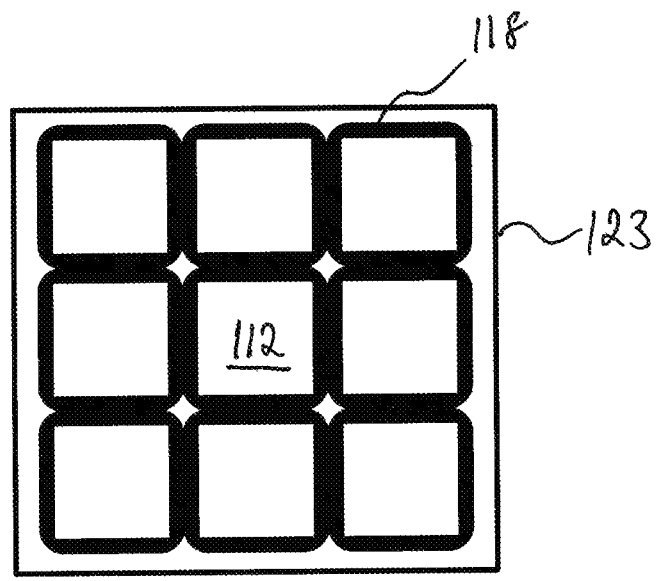
FIG. 5B is a schematic cross-section view showing the packing of bands in a catheter comprising a shaft having a rectangular-shaped lumen, in accordance with an embodiment.

FIGS. 5A and 5B are schematic cross-section views showing the packing of bands in catheters comprising shafts having different shaped lumens. FIG. 5A shows a circular shaped lumen 121 and FIG. 5B shows a rectangular shaped lumen 123. The substantially rectangular cross-sections of the bands 112 and wire coils 118 permit at least some of the bands to be packed more closely in the catheter when the frame is constrained in its compressed configuration. The rectangular cross-sections of the bands and wire coils also permit a higher density of bands to be packed in the catheter with reduced empty space between adjacent bands when the frame is constrained in its compressed configuration. The wrapping of the wire coils around the bands to achieve certain predetermined thicknesses can be advantageous in improving the packing of the bands, since it reduces empty space between adjacent compressed bands while providing structural reinforcement to the bands. Referring to FIGS. 5A and 5B, a greater volume of each lumen can be filled using bands and coils having rectangular cross-sections compared to similar bands and coils having circular cross-sections. In some embodiments, the amount of empty space in the lumen can be reduced by at least 5%, 10%, 15%, 20%, 25%, 30%, or any value therebetween, when using bands and coils that have rectangular cross-sections instead of circular cross-sections.

Figure 6A:
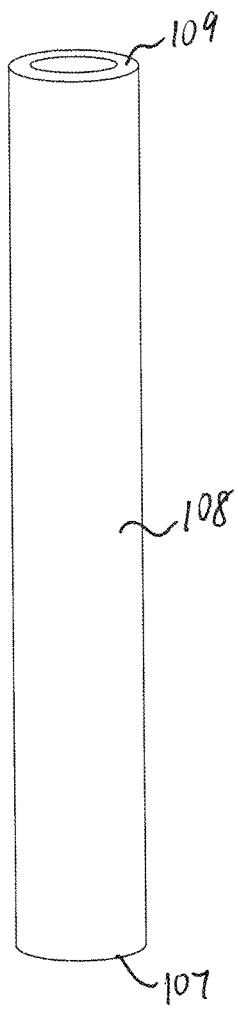

FIGS. 6A-6G illustrate a method of forming a vascular cage in accordance with an embodiment. Initially, a tube 108 is provided (FIG. 6A). The tube may comprise a first end 109 and a second end 107 located at opposite distal ends. The tube may be extruded from a monolithic block of material having super-elastic and shape memory material properties. In some embodiments, the tube may comprise an elongated nitinol tube.

Figure 6B:
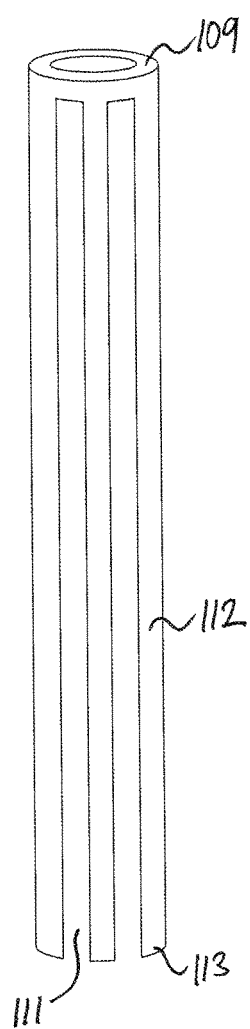

Next, the tube may be laser cut, chemically etched, or otherwise patterned to form a plurality of elongated flexible bands 112 (FIG. 6B). For example, slots 111 can be cut along the length of the tube to form the bands. The bands may remain connected at the uncut first end 109 of the tube. Distal ends 113 of the bands may be cut free from each other at the second end 107 of the tube such that the bands hang freely from the uncut first end in an elongated manner. At least some of the plurality of bands may have a substantially rectangular cross-section as described elsewhere herein.

Figure 6C:
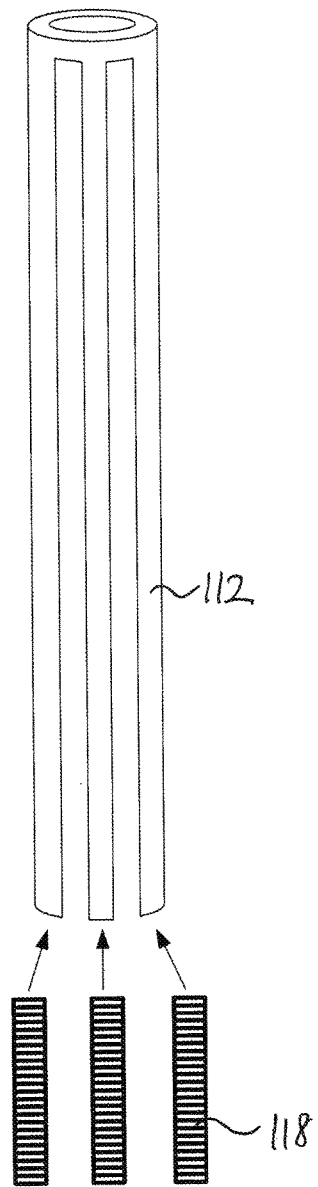
Figure 6D:
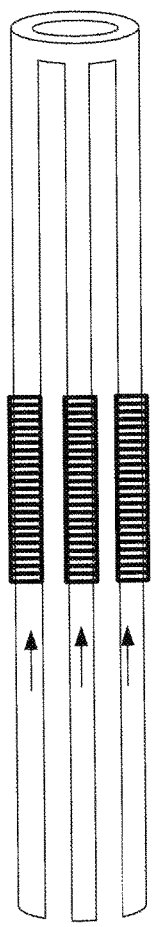

Next, a wire coil 118 may be loaded over an open end of at least some of the bands 112 (FIG. 6C). In some cases (not shown), the free-hanging ends of the bands may be splayed apart to create space for aiding insertion of the wire coils. The wire coils may comprise a substantially rectangular shaped cross-section, and may be configured to wrap around a portion of the bands. The wire coils may comprise a radio opaque material as described elsewhere herein. The wire coils can be moved to predetermined locations along the bands, for example by sliding along the bands (FIG. 6D).

After the wire coils are moved to predetermined locations along the bands, the free-hanging bands may be compressed (FIG. 6E) such that the bands splay out into an expanded configuration (FIG. 6F). The expanded configuration may be generally spherical or ovoid. In some embodiments, the expanded configuration may include a dimpled portion near the uncut first end of the tube. The distal ends 113 of the bands may be placed in proximity to each other in the expanded configuration. The frame may be formed by placing the distal ends of the elongated flexible bands in proximity with each other and connecting the distal ends using an attachment material 119 (FIG. 6G). Exemplary means of the attachment material may include solders, welds, adhesives, epoxies, glues and the like. The frame may be a self-expandable frame, and can be configured to transition between a compressed configuration and an expanded configuration as described elsewhere herein. The expanded frame can form a three-dimensional cage configured to occupy and/or surround an interior volume within a vascular aneurysm, blood vessel lumen, or the like, as the frame is deployed.

The method of FIGS. 6A-6G may be modified in accordance with various embodiments. In one embodiment, instead of freeing the distal ends of the bands, the tube may be laser cut, chemically etched, or otherwise patterned such that the bands remain connected at an uncut second end of the tube. The uncut second end may be located opposite to the first uncut end of the tube. The wire coils may be modified such that they can be wrapped around the bands without requiring insertion over open ends of the bands. For example, a wire coil may include two or more separate coils that can be detachably coupled together to wrap around a portion of a band.

In some embodiments, the tube shown in FIG. 6A may be laser cut, chemically etched, or otherwise patterned such that the bands are fully separated from each other, without an uncut end of the tube to connect and hold the bands together. In these embodiments, a wire coil may be loaded over an open end of one or more individual bands to wrap around a portion of the bands. A frame may be formed by connecting first ends of the individual bands to each other at a first location and connecting second ends of the individual bands to each other at a second location. The frame may be a self-expandable frame similar to that shown in FIG. 6G.

In some embodiments, at least one band may comprise a cross-section having varying shape, size, area, and/or longitudinal thickness profile. Additionally or optionally, a band may comprise a first end having a different cross-sectional shape than a second end. The cross-section having the varying shape, size, area, and/or longitudinal thickness profile may be formed by preferential etching of the band.

In some embodiments, a band may comprise a tapered profile. The tapered profile may be formed by laser cutting, chemically etching, or otherwise patterning a tube of material described elsewhere herein. The tapered profile may be formed on a portion of the band, for example at or near a distal end of the band. Alternatively, the tapered profile may be formed along an entire length of a band. In some cases, the tapered profile may be formed on different portions of a band. For example, a band may comprise a plurality of tapered portions spaced longitudinally apart along a length of the band. The plurality of tapered portions may each have the same length or different lengths. The plurality of tapered portions may each have the same width or different widths. The plurality of tapered portions may each have the same thickness or different thicknesses. The plurality of tapered portions may each have the same tapering profile or different tapering profiles. Tapering profile(s) may be generated along one or more dimensions of a band (e.g., length, width, thickness, diameter, or cross-sectional area of a band). In some embodiments, a taper angle and/or width of the tapering profile(s) may be designed to achieve one or more of the following: (1) permit ease of manufacturing, (2) improve structural rigidity of the band(s), or (3) define the gaps/spacing between adjacent bands which may influence packaging of the bands in a catheter.

Figure 7A:
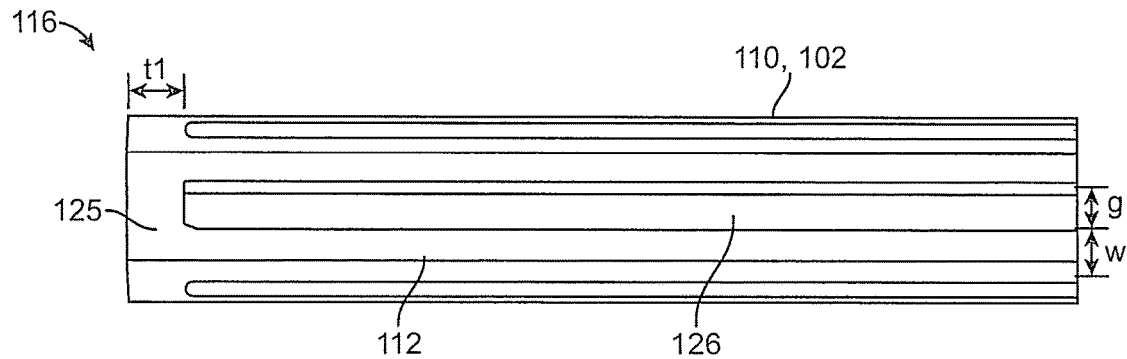
FIGS. 7A and 7B show different locations of a self-expandable frame in its compressed configuration, in accordance with some embodiments.
Figure 7B:
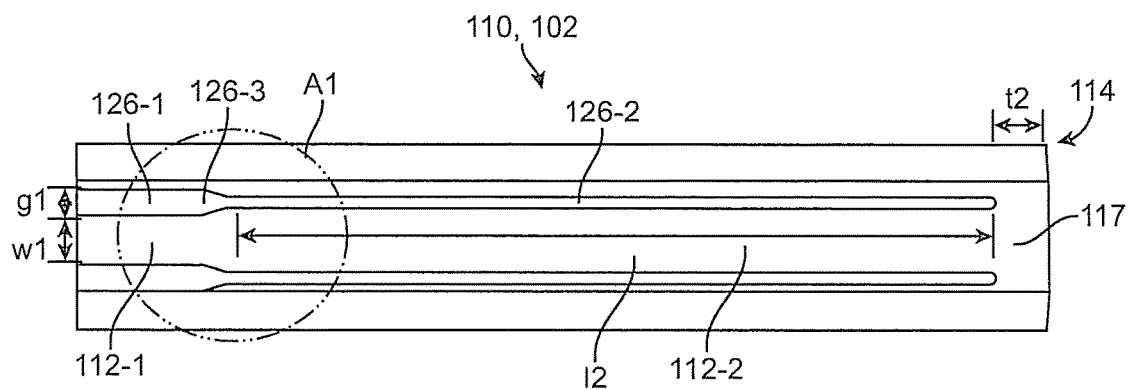

In some embodiments, a tapered profile may be formed at one or more ends of a band. For example, a band may have a tapered profile near its distal end. A proximal end of the band may or may not have a tapered profile. FIGS. 7A and 7B respectively show a second location 116 and a first location 114 of a self-expandable frame 110 in its compressed configuration 102, in accordance with some embodiments. The frame may include a plurality of bands 112 spaced apart by gaps 126. A gap may have a width g. One or more of the bands may have a tapered profile or a tapered portion. The distal ends of the bands may be provided at the first location 114, and the proximal ends of the bands may be provided at the second location 116. As shown in FIG. 7A, the proximal ends of the bands 112 may be connected via a ring 125. A thickness of the ring 125 may be given by t1. The bands may have a non-tapered profile near the second location 116 such that a width w of each band is substantially uniform as it extends longitudinally away from the ring 125. The non-tapered profile may extend from the proximal ends of the bands towards the distal ends of the bands. In some embodiments, the width w of a band may be substantially uniform along its length until it reaches the tapered profile shown in FIG. 7B. The tapered profile may be located near the first location 114 of the frame. The tapered profile may be provided near the distal ends of the bands 112. For example, the tapered profile (corresponding to a section where the bands start to widen or narrow) may be located at a distance from the ring 117. As shown in FIG. 7B, the distal ends of the bands 112 may be connected via ring 117 described elsewhere herein. A thickness of the ring 117 may be given by t2. In some embodiments, the thicknesses t1 and t2 of the rings 117 and 125 may be the same. Alternatively, the thicknesses t1 and t2 of the rings 117 and 125 may be different. In some embodiments, the thicknesses t1 and t2 may be customized to achieve a desired rigidity at the first and second locations 114 and 116 of the frame. The desired rigidity may be determined based on the bending at the first and second locations of the frame, which are typically subject to large amounts of bending as the frame deploys from the compressed configuration to its expanded configuration.

Figure 7C:
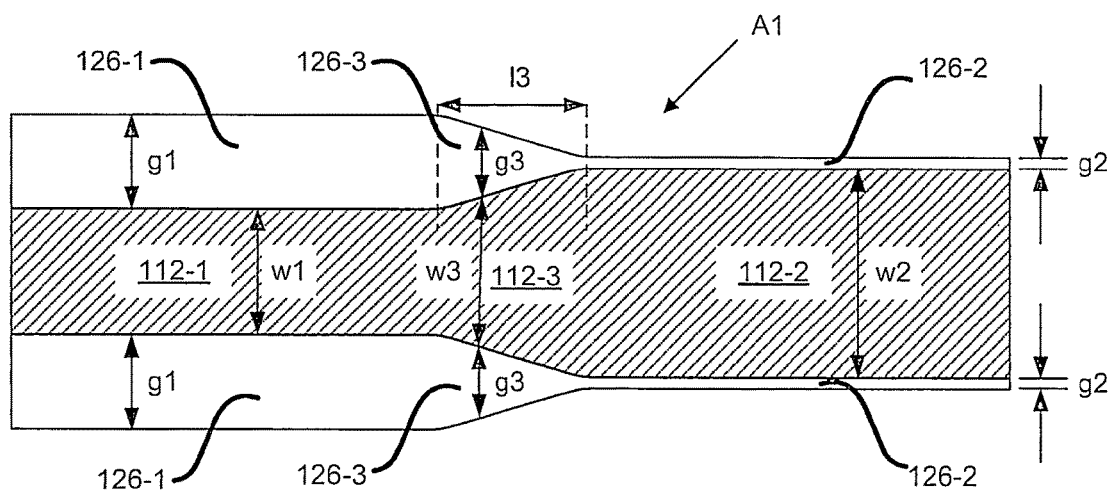
FIG. 7C shows a magnified schematic view of the tapered profile (section A1) of FIG. 7B.

FIG. 7C shows a magnified schematic view of the tapered profile (section A1) of FIG. 7B. The tapered profile may result in a band having different widths along its length. A band may be wider near its distal end, and may narrow with increasing distance away from the distal end. For example, as shown in FIGS. 7B and 7C, a band 112 may comprise a first portion 112-1 having a width w1. The width w1 may have the same value or a different value from the width w shown in FIG. 7A. The first portions 112-1 of the bands may be spaced apart by a gap 126-1. The gap 126-1 may have a width g1, which may have the same value or a different value from the width g shown in FIG. 7A. In some embodiments, the first portion 112-1 may extend longitudinally from the second location 116 of the frame to the tapered profile.

The band may also comprise a second portion 112-2 having a second width w2 along a predetermined length l2 near the first location 114 of the frame. The second portion 112-2 of the band may be wider/thicker than the first portion 112-1. The second portions 112-2 of the bands may be spaced apart by a gap 126-2. The gap 126-2 may be smaller than the gap 126-1.

The first and second portions may be connected via a third portion 112-3 having the tapered profile. As shown in FIG. 7C, a width w3 of the tapered profile may vary such that it changes (increases) from w1 to w2 along a length l3 between the first portion 112-1 and the second portion 112-2. In some embodiments, the length l2 of the second portion 112-2 of the band may be predetermined based on a length of a coil (e.g. coil 118) overlaid onto the band. The tapered profile may permit the overlaid coil to fit better over the band when the cage is in the catheter, and when a plurality of overlaid coils are laid close to one another. Generally, thinner bands can aid in providing a more flexible deployed cage. The thicker second portion 112-2 (having the second width w2) near the distal ends of the bands can help to structurally reinforce and stabilize the cage at a location where it may bend the most (e.g., near the dimpled portion 115 described elsewhere herein). In some embodiments, the width w1 of the first portion 112-1 of the band may range from about 0.0005" to about 0.0025", preferably 0.001" to 0.002". A range of values may be contemplated for the width w2 of the second portion 112-2 of the band, the length l1 (not shown) of the first portion 112-1, the length l2 of the second portion 112-2, and the length l3 of the third portion 112-3 (having the tapered profile), and can be configured based on design requirements (e.g. size, flexibility, and/or shape of the self-expandable frame).

As previously described, the different widths of the bands can result in different sized gaps/spacing between adjacent bands. For example, as shown in FIG. 7C, the gap 126-2 (having a width g2) between the second portions 112-2 of the bands may be larger than the gap 126-1 (having a width g1) between the first portions 112-1 of the bands. A gap 126-3 between the third portions 112-3 of the bands may have a tapered profile inverse to that of the third portions.

For example, as shown in FIG. 7C, a width g3 of the gap 126-3 may gradually decrease from g1 to g2 towards the distal ends of the bands.

Figure 8A:
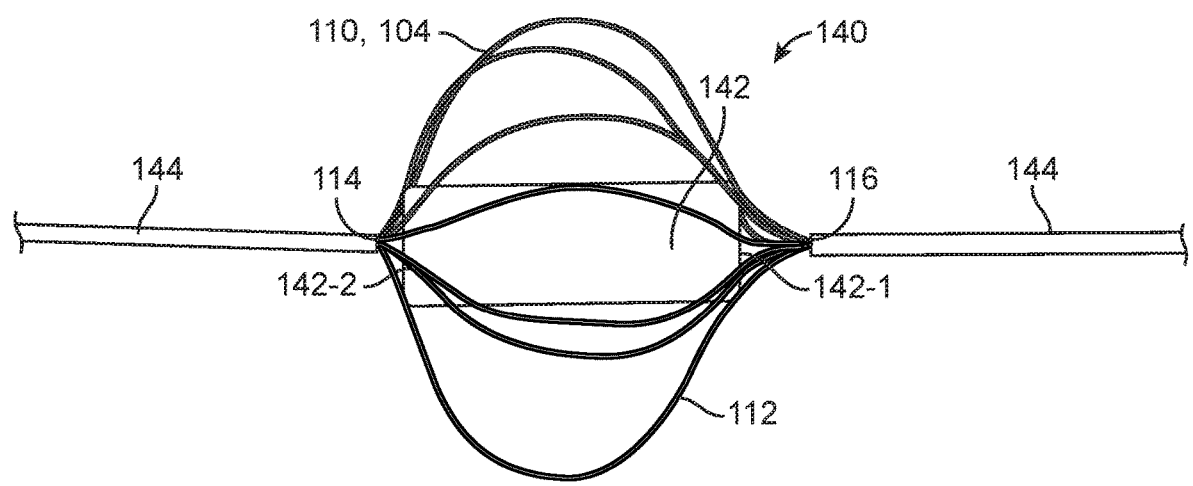
FIGS. 8A and 8B illustrate a shape setting apparatus for forming a self-expandable frame having a dimpled portion in its expanded configuration, in accordance with some embodiments.
Figure 8B:
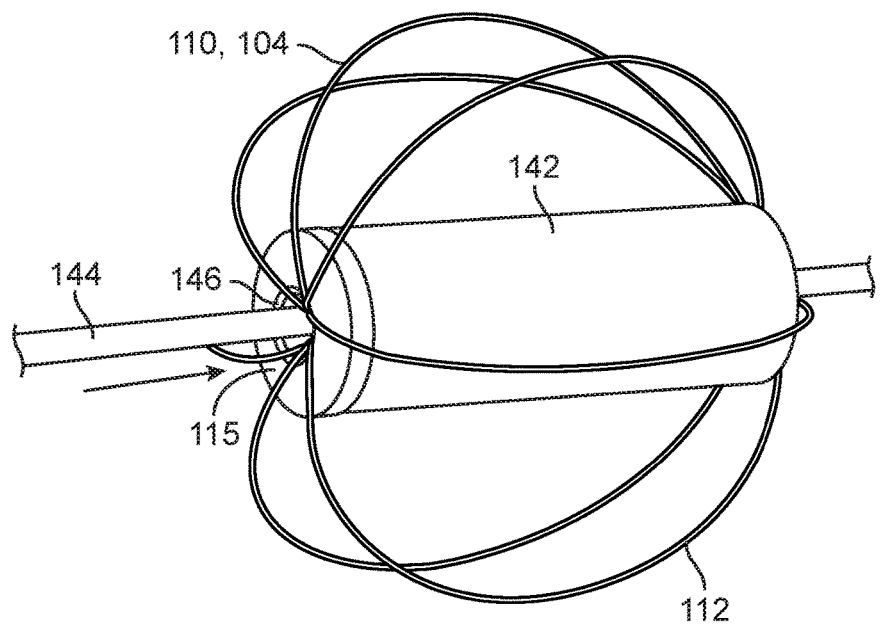

As previously described, a self-expandable frame may be generally spherical or ovoid in its expanded configuration. In some cases, the self-expandable frame may comprise at least one dimpled portion in its expanded configuration. FIGS. 8A and 8B illustrate an example of a shape setting apparatus 140 for forming a self-expandable frame having a dimpled portion in its expanded configuration. The shape setting apparatus 140 may comprise an expansion device 142. Referring to FIG. 8A, the expansion device 142 may be placed into the frame 110, with a proximal end 142-1 and a distal end 142-2 of the device supporting and pushing out the proximal and distal ends of the bands in order to expand the frame. The frame may be expanded to a generally ovoid shape. The expansion device 142 may be cylindrical in shape, although the invention is not limited thereto. For example, the expansion device may be provided in different shapes and/or sizes depending on the desired shape and/or size of the expanded frame.

In some embodiments, the shape setting apparatus 140 may comprise one or more end rods 144 that can be used to form a dimpled portion in the expanded frame. For example, referring to FIGS. 8A and 8B, the end rods 144 may be placed at the opposite ends of the frame 110 (e.g. at the first location 114 and the second location 116). The expansion device 142 may include a cavity 146 at one or more ends of the device. As shown in FIG. 8B, a dimpled portion (e.g. 115) can be formed by using an end rod 144 to push an end portion of the expanded frame 110 into the cavity 146 of the expansion device. The size and/or depth of the dimpled portion 115 can be controlled based on the size and/or depth of the cavity 146. For example, a deeper cavity can be used to form a more pronounced flattened, ovoid shape, whereas a shallower cavity can be used to form a more spherical shape. The size and/or depth of the dimpled portion can also be controlled by controlling an amount by which the end portion of the frame is pushed into the cavity of the expansion device. For example, pushing the end portion of the frame into the cavity by a greater amount can result in a more pronounced dimpled portion, whereas pushing the end portion of the frame into the cavity by a lesser amount can result in a less pronounced dimpled portion. After the expanded frame 110 with dimpled portion 115 has been formed, the end rod 144 may be retracted away from the cavity 146 of the expansion device 142, and the expansion device may then be removed from the frame. Due to the super-elastic and shape memory material properties of the bands 112, the expanded frame 110 with dimpled portion continues to maintain its shape even after the expansion device and end rod have been removed.

Figure 9A:
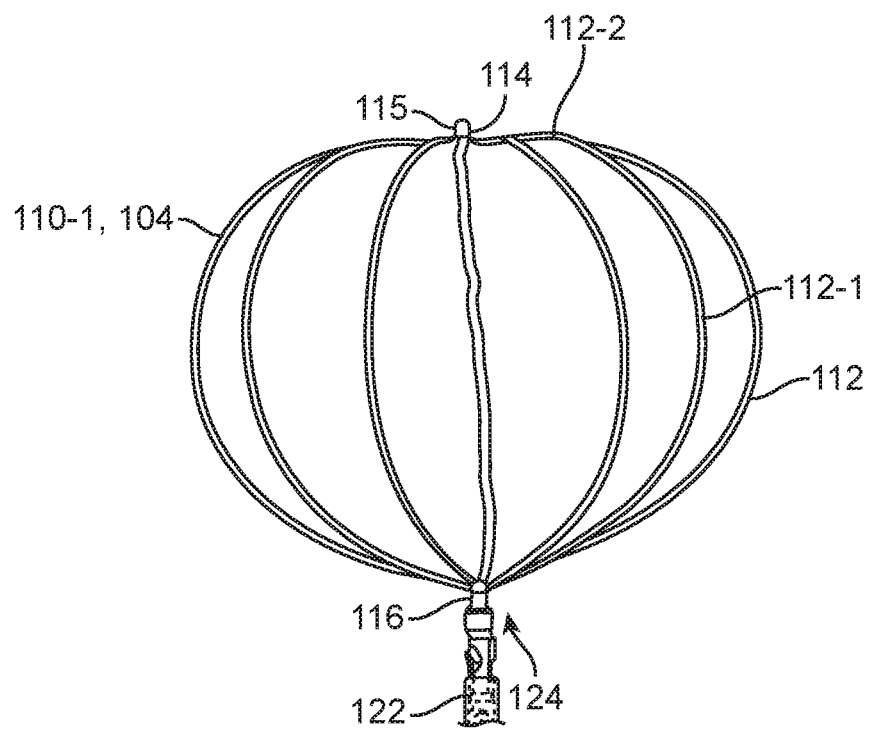
FIG. 9A shows a vascular cage comprising a self-expandable frame having a generally spherical or ovoid shape in its expanded configuration, in accordance with some embodiments.

FIG. 9A illustrates a vascular cage comprising a self-expandable frame 110-1 having a generally spherical or ovoid shape in its expanded configuration 104, in accordance with some embodiments. The bands may include first portions 112-1 and second portions 112-2. In some embodiments, a width of the first portions 112-1 may preferably be about 0.0031", and a wall thickness of the first portions 112-1 may preferably be about 0.0013". A width of the second portions 112-2 may preferably be about 0.0045", and a wall thickness of the second portions 112-2 may preferably be about 0.0013". It should be noted that the above dimensions are merely exemplary and that any values may be contemplated.

Figure 9B:
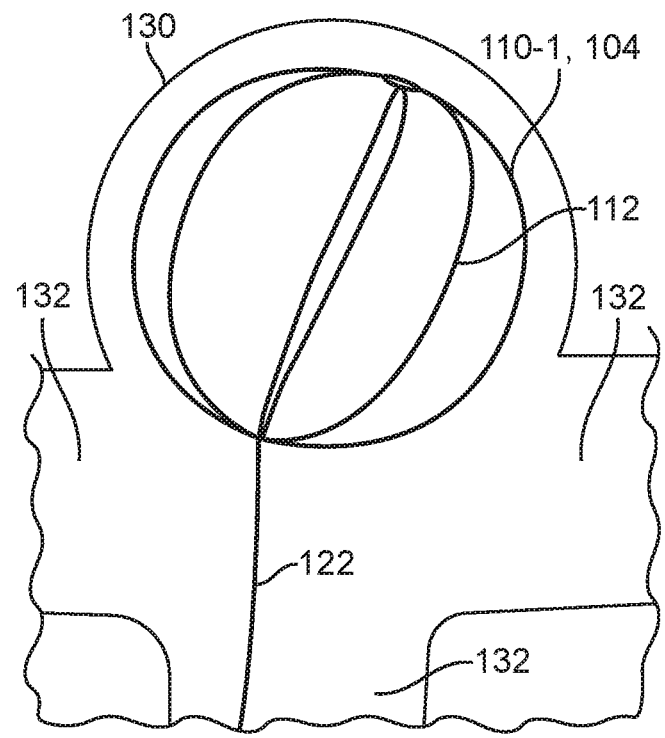
FIG. 9B shows an X-ray of the expanded frame of FIG. 9A in an aneurysm flow model.

The first location 114 of the expanded frame may have a dimpled portion 115 as described elsewhere herein. In the example of FIG. 9A, the second location 116 of the expanded frame may have a generally convex shape, and may not have a dimpled portion. The second location 116 of the frame may be coupled to a pusher 122 via a deployment junction 124 described elsewhere herein. FIG. 9B illustrates an X-ray of the expanded frame 110-1 of FIG. 9A in an aneurysm flow model. The cage can be delivered through vasculature 132 to a target location which may be an aneurysm 130. The expanded frame 110-1 can form a three-dimensional spherical or ovoid cage configured to occupy and/or surround an interior volume within the aneurysm as the frame is deployed. For example, the expanded frame 110-1 can be configured to frame an interior of the aneurysm, thereby providing an cage in the aneurysm. The three-dimensional spherical or ovoid cage can provide an interior unobstructed space allowing one or more smaller filling coils to be subsequently deployed therein. In the example of FIGS. 9A and 9B, the bands of the frame may possess sufficient rigidity such that the bands maintain their alignment/spacing when the cage is provided and deployed in the aneurysm, and are unaffected by the deployment or by flow of fluids in the aneurysm.

Figure 10A:
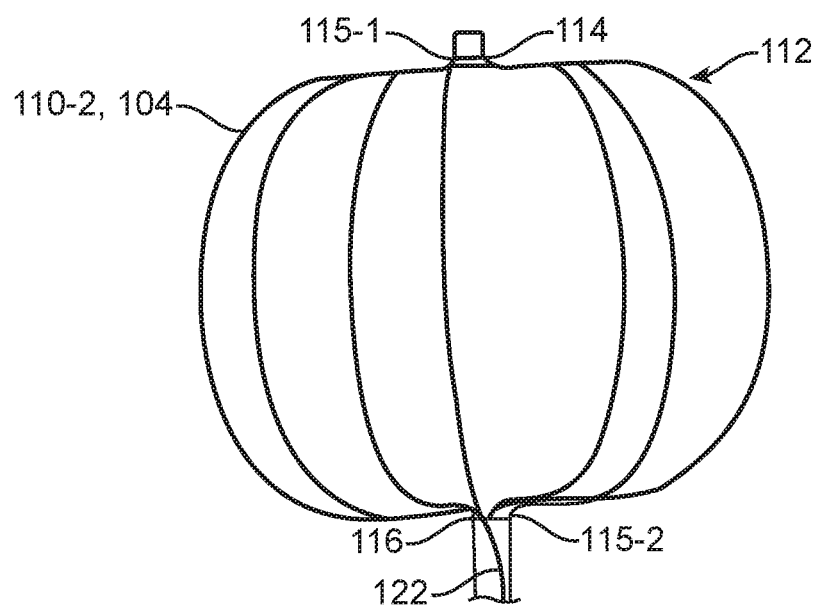
FIG. 10A illustrates an cage comprising a self-expandable frame having a flattened ovoid shape in its expanded configuration, in accordance with some embodiments.
Figure 10B:
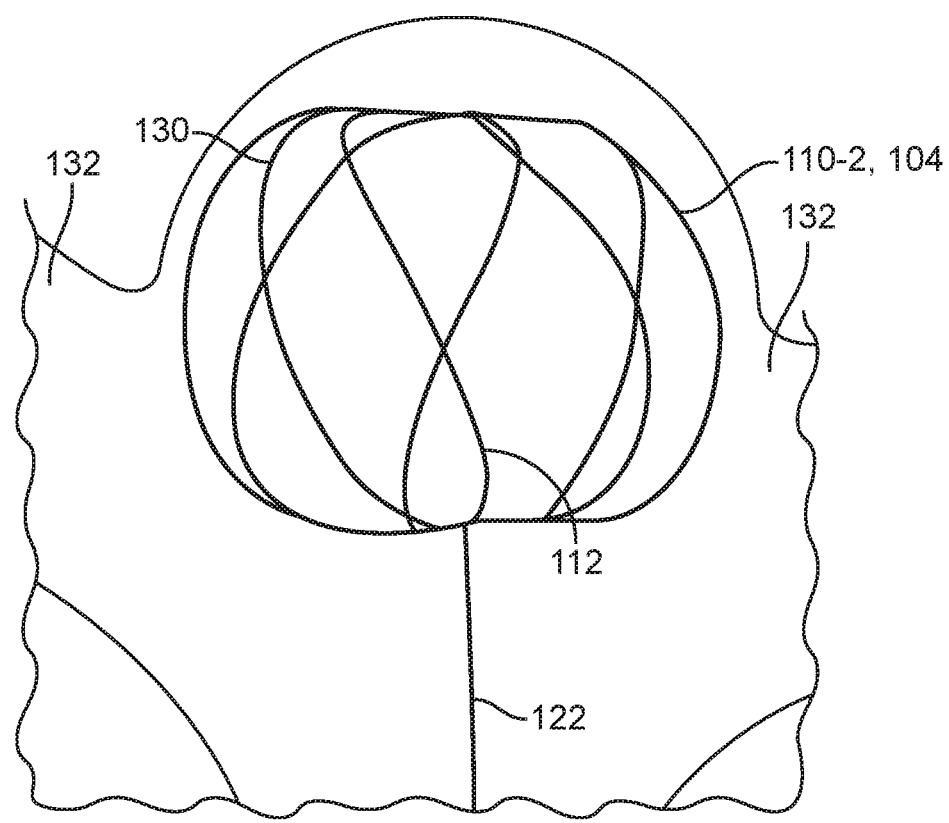
FIG. 10B illustrates an X-ray of the expanded frame of FIG. 10A in an aneurysm flow model.

FIG. 10A illustrates a vascular cage comprising a self-expandable frame 110-2 having a flattened ovoid shape in its expanded configuration 104, in accordance with some embodiments. The frame 110-2 may comprise a first dimpled portion 115-1 at the first location 114, and a second dimpled portion 115-2 at the second location 116. The second location 116 of the frame may be coupled to a pusher 122 as described elsewhere herein. FIG. 10B illustrates an X-ray of the expanded frame 110-2 of FIG. 10A in an aneurysm flow model. The cage can be delivered through vasculature 132 to a target location which may be an aneurysm 130. The expanded frame 110-2 can form a three-dimensional flattened ovoid cage configured to occupy and/or surround an interior volume within the aneurysm as the frame is deployed. For example, the expanded frame 110-2 can be configured to frame an interior of the aneurysm, thereby providing a frame in the aneurysm. In some embodiments, the bands in the frame of FIGS. 10A and 10B may be more flexible compared to the bands in FIGS. 9A and 9B. For example, FIG. 10A shows the bands 112 extending along meridians of the expanded frame 110-2 between opposite locations of the frame. When the cage is provided and deployed in the aneurysm, the bands 112 in FIG. 10B may flex to a greater degree compared to the bands in the example of FIG. 10A, as visible in a comparison between FIGS. 10A and 10B. The increased flexibility may allow use of the device in a wider range of sizes of aneurysm. As an example, the feature safely permits oversizing of the device. In some cases, the bands may be permitted to move/flex resulting from flow of fluids in the aneurysm.

The cage and self-expandable frame in any of the embodiments described herein can be used as part of a system for occluding a vascular location. In some embodiments, a method of occluding a vascular location may comprise providing an cage, delivering the cage while constrained in its compressed configuration to a target site in the vasculature, releasing the cage from constraint so that it expands to its expanded configuration at the target location, and thereafter delivering embolic coils to the site.

The cage can be delivered by positioning a distal end of a cage delivery catheter at a target location in a patient's vascular, and advancing the cage in its compressed configuration through a lumen of the cage delivery catheter. The target location may be an aneurysm. Optionally, the target location may be a blood vessel lumen. The vascular cage can be released from constraint by releasing the cage from the distal end of the cage delivery catheter so that the cage self-expands at the target location. In some embodiments, the method of occluding the vascular location may further comprise delivering coils into the interior volume of the cage after the cage has been released.

FIGS. 11A through 11E illustrate a shape setting apparatus 180 for manufacturing a vascular cage in accordance with other embodiments. The apparatus 180 can be used to form a self-expandable frame having a dimpled portion in its expanded configuration. The shape setting apparatus 180 may comprise an expansion device 182 which may have a barrel shape. The expansion device may be provided in different shapes and/or sizes depending on the desired shape and/or size of the expanded frame.

Figure 11A:
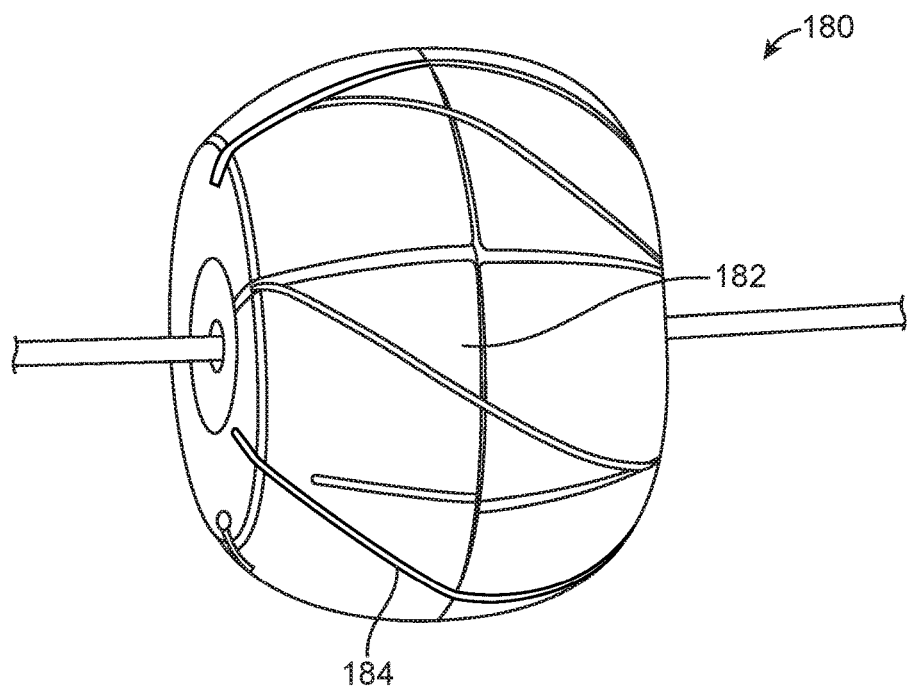
FIGS. 11A-11E illustrate a shape setting apparatus for forming a self-expandable frame in accordance with some alternative embodiments.

As shown in FIG. 11A, a plurality of bands 184 are wrapped around the expansion device 184. In some embodiments, the bands 184 may be wrapped closely around the expansion device 184 at an oblique angle to a longitudinal axis extending between opposite ends of the barrel-shaped expansion device. In contrast, in the embodiment illustrated in FIGS. 8A and 8B, the bands 104 generally extend away and outward from the expansion device 142, in an arc-like manner longitudinally from one end of the expansion device 142 to the other end of the expansion device.

Figure 11B:
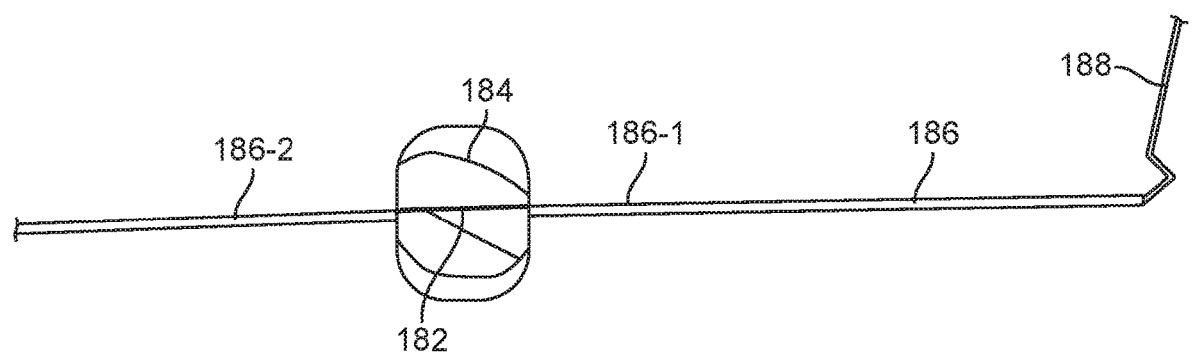

Referring to FIG. 11B, the apparatus 180 may include a shape set hypotube 186 operably coupled to the expansion device 182. For example, the shape set hypotube 186 may be inserted into a through-hole extending along a longitudinal axis of the expansion device 182. The shape set hypotube 186 may include a proximal portion 186-1 extending from one end of the expansion device 182, and a distal portion 186-2 extending from another end of the expansion device 182. A mandrel 188 may be inserted from the proximal portion 186-1 through the expansion device 182 and the distal portion 186-2. In some embodiments, the mandrel 188 may be made of stainless steel although the invention is not limited thereto. A plurality of bands 184 may be inserted from the proximal portion 186-1 of the shape set hypotube 186 and wrapped around the expansion device 182. The mandrel 188 may include end portions extending beyond the proximal and distal portions of the shape set hypotube 186. The end portions of the mandrel 188 may be bent and used to support the expansion device 182 as the bands 184 are being wrapped around the expansion device 182.

Figure 11C:
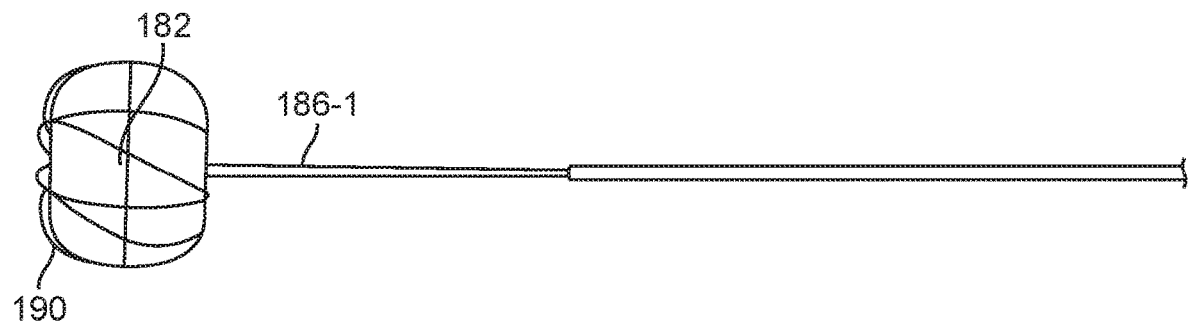
Figure 11D:
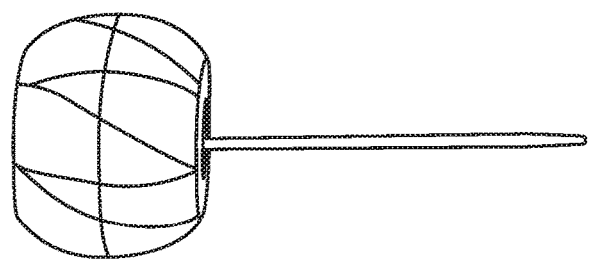
Figure 11E:
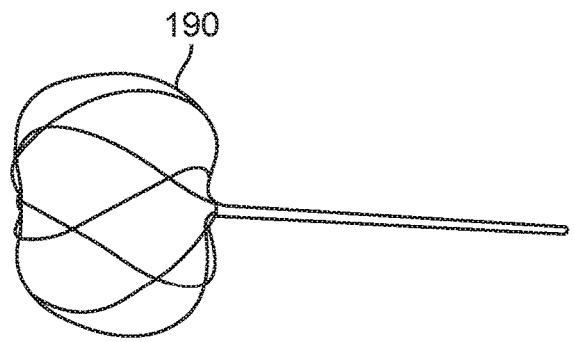

After a frame 190 has been formed (by wrapping the bands 184 around the expansion device 182), the two bent ends of the mandrel 188 and the proximal and distal portions 186-1/186-2 of the shape set hypotube may be cut, in order to allow removal/release of the frame 190 from the expansion device 182. FIG. 11C shows the distal portion 186-2 and the corresponding mandrel 188 having been cut, leaving in place the proximal portion 186-1 of the shape set hypotube 186. Any unused portion of the bands 184 may be removed via the proximal portion 186-1 of the shape set hypotube 186. FIG. 11D shows the unused portion of the bands 184 having completely been removed from the the proximal portion 186-1 of the shape set hypotube 186. Subsequently, the frame 190 can be completely removed from the expansion device 182, as shown in FIG. 11E. Due to the super-elastic and shape memory material properties of the bands 184, the frame 190 continues to maintain its shape even after the expansion device has been removed.

Figure 12A:
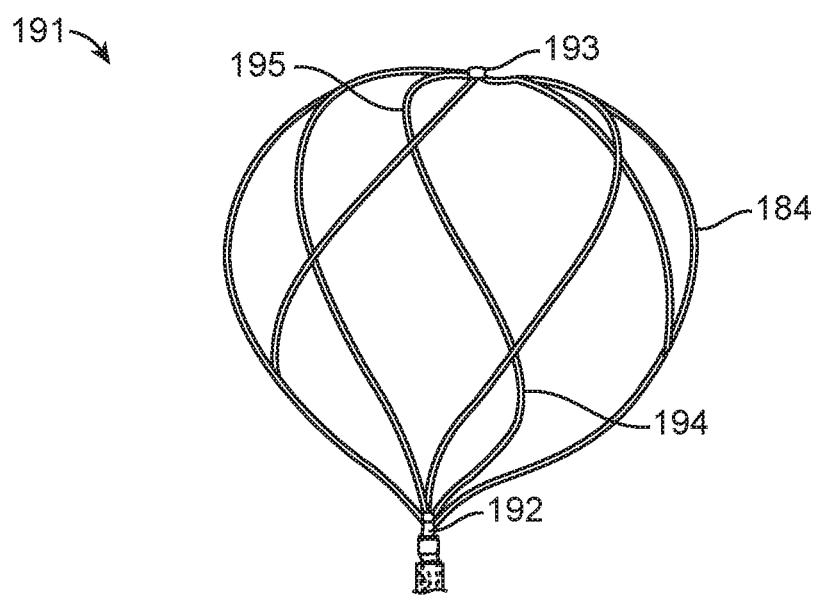
FIG. 12A shows a vascular cage constructed using the shape setting apparatus of FIGS. 11A-11E in accordance with an embodiment.

FIG. 12A shows a vascular cage 191 fabricated using the expansion device 182 of FIG. 11. The vascular cage 191 is shown in its deployed configuration. A plurality of bands 184 may extend obliquely from a proximal end 192 to a distal end 193 of the cage. In some embodiments, the bands 184 may further comprise bends 194 and 195. The structure of the cage 191 may provide greater flexibility and latitude in sizing of the device to fit a wider range of sizes of aneurysms.

Figure 12B:
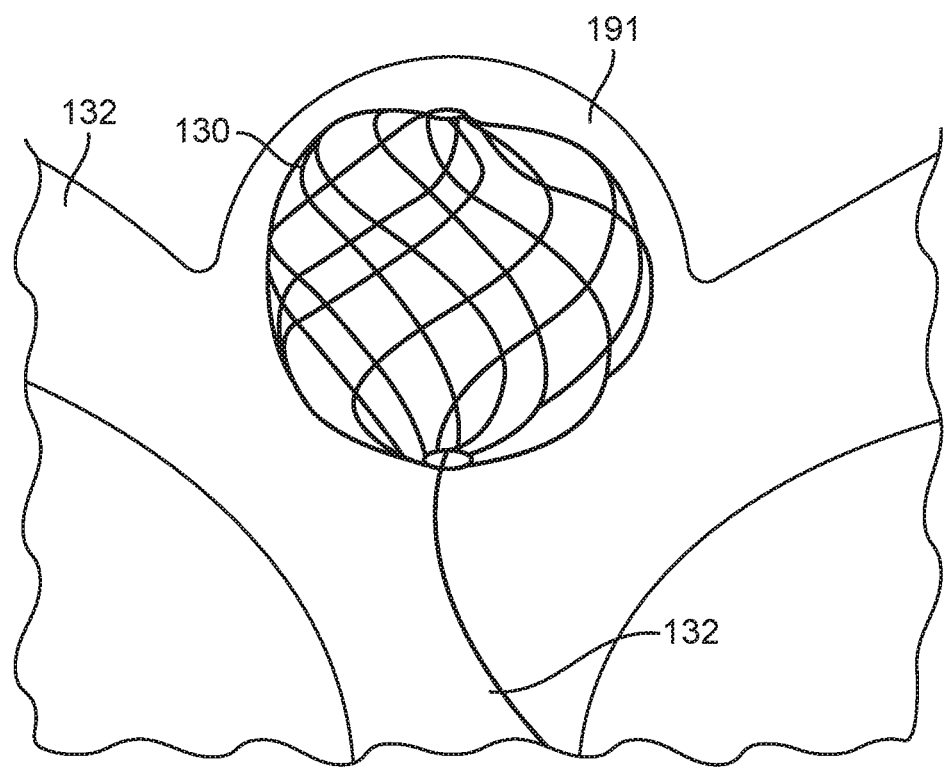
FIG. 12B shows an X-ray of multiple vascular cages constructed using the shape setting apparatus of FIGS. 11A-11E, the vascular cages being deployed in an aneurysm flow model.

FIG. 12B illustrates an X-ray of multiple frames 191 or cages fabricated in a similar manner to the embodiments of FIGS. 11A-11E and 12A, that are shown deployed in an aneurysm flow model. The frames can be delivered through vasculature 132 to a target location which may be an aneurysm 130. The expanded frames 191 can be configured to occupy and/or surround an interior volume within the aneurysm as the frames are deployed. The increased flexibility may allow use of the device in a wider range of sizes of aneurysm. As an example, the feature safely permits oversizing of the device. In some cases, the bands may be permitted to move/flex resulting from flow of fluids in the aneurysm.

Figure 13A:
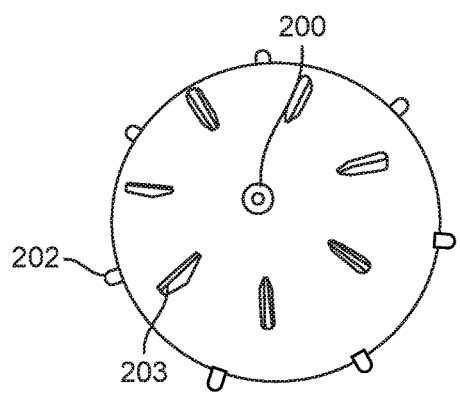
FIGS. 13A and 13B show a shape setting apparatus that can be used to manufacture vascular cages in accordance with other embodiments.
Figure 13B:
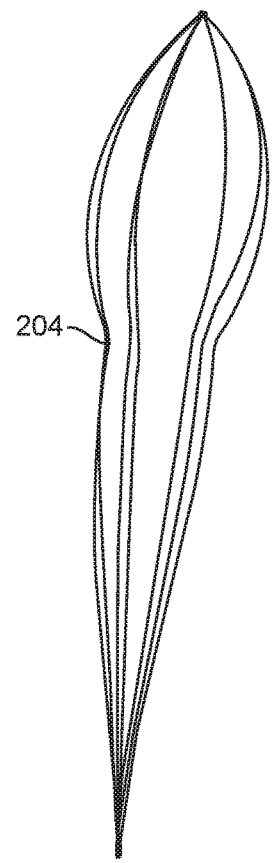
Figures 13C, 13D:
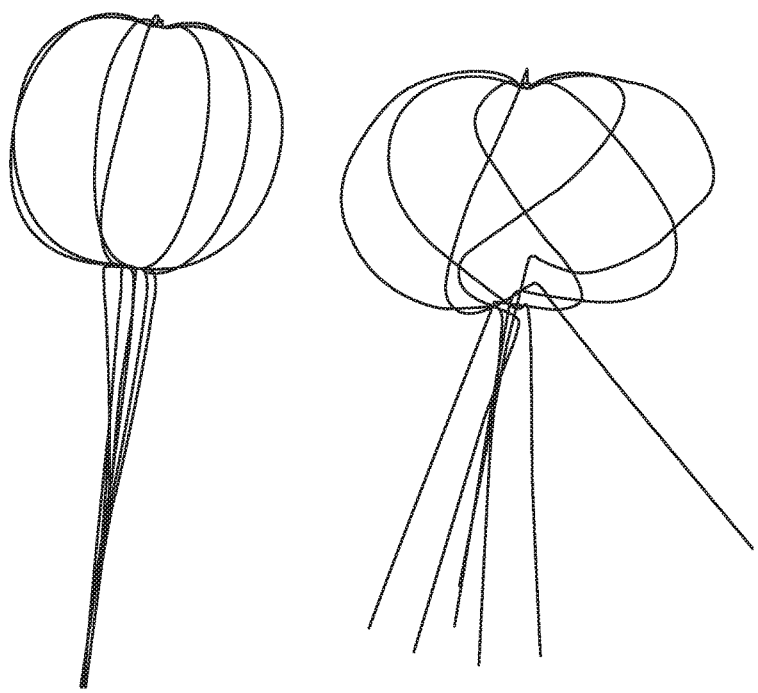
FIGS. 13C-13E show cages formed using the shape setting apparatus of FIGS. 13A and 13B, and having a variety of different shapes, bends and sizes.
Figure 13E:
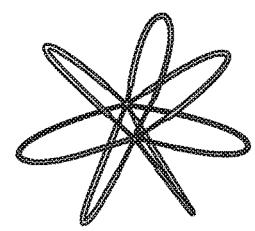

FIGS. 13A and 13B illustrate a shape setting apparatus that can be used to manufacture vascular cages having a variety of different shapes, bends and sizes (e.g. FIGS. 13C-13E) in accordance with other embodiments. Referring to FIG. 13A, the shape setting apparatus may be a shape setting sphere 200. The shape setting sphere 200 may include protrusions 202 extending circumferentially around the great circle of the sphere (where the diameter is the greatest). Additionally or optionally, the shape setting sphere may include protrusions 203 extending on other portions of the sphere (e.g. upper hemispherical portion or lower hemispherical portion). The protrusions can be configured to hold cages in place during a heating stage to induce S-shaped bends. FIG. 13B illustrates a plurality of bands 204 as described elsewhere herein. The bands 204 may be connected at opposite ends (eg. proximal and distal ends). The bands 204 may be wrapped around the shape setting sphere 200 to form a variety of cages of different shapes and bends, for example as shown in FIGS. 13C-13E. In some embodiments, a bottom end of a cage may be cut such that proximal ends of the bands are cut free from each other. A free end of one or more bands may be inserted into a lumen of one or more wire coils, and then the coil may be moved along the bands to a predefined location, prior to joining the free/open ends of the bands. In some embodiments, the wire coils may include radio-opaque markers. When the wire coils and/or markers are in location, the open ends of the bands can be connected using any attachment material such as solders, welds, adhesives, epoxies, glues and the like. A ball for a release joint may be attached as described elsewhere herein.

Although certain embodiments and examples are provided in the foregoing description, the inventive subject matter extends beyond the specifically disclosed embodiments to other alternative embodiments and/or uses, and to modifications and equivalents thereof. For example, the apparatus and methods described herein can be applied to any type of vaso-occlusive devices or methods for making or using such devices. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

As used herein A and/or B encompasses one or more of A or B, and combinations thereof such as A and B. It will be understood that although the terms "first," "second," "third" etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present disclosure.

The terminology used herein is for the purpose of describing particular embodiments only and is not intended to limit the present disclosure. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the described embodiments will be apparent to a person skilled in the art. It is therefore contemplated that the invention shall also cover any such modifications, variations and equivalents.

What is claimed is:

1. A vascular cage comprising:
   a self-expandable frame including a plurality of elongated flexible bands connected to each other at opposite ends of the frame, said frame being configured to transition between a compressed configuration and an expanded configuration, wherein the expanded frame forms a three-dimensional cage configured to surround an interior volume as the frame is deployed, wherein at least some of the plurality of bands have a substantially rectangular cross-section; and wherein the plurality of bands, when in the compressed configuration, together form a rectangular cross-section;
   a pusher wire having an attachment fixture thereon; and
   a severable deployment junction located at proximal ends of the plurality of bands releasably connecting each of said plurality of bands to said pusher wire.

2. An occlusive system comprising:
   the vascular cage of claim 1; and
   a cage delivery catheter having a lumen configured to constrain the self-expandable frame in its compressed configuration and to release the self-expandable frame into a target location in a vasculature in its expanded configuration, wherein the lumen of the cage delivery catheter has a substantially rectangular cross-section.

3. The vascular cage of claim 1, wherein at each of the plurality of the bands comprises a first bend when said frame is in its expanded configuration.

4. The vascular cage of claim 1, wherein the substantially rectangular cross-section allows at least some of the plurality of bands to be packed more closely relative to a circular cross-section in a cage delivery catheter when the self-expandable frame is constrained in its compressed configuration in said catheter.

5. The vascular cage of claim 1, wherein the substantially rectangular cross-section allows a higher density of bands relative to a circular cross-section to be packed in a cage delivery catheter with reduced empty space between adjacent bands when the self-expandable frame is constrained in its compressed configuration in said catheter.

6. The vascular cage of claim 1, wherein at least one band comprises a cross-section having varying shape, size, area, and/or longitudinal thickness profile.

7. The vascular cage of claim 6, wherein said band comprises a first end having a larger cross-sectional area than a second end.

8. The vascular cage of claim 6, wherein said band comprises a first end having a different cross-sectional shape than a second end.

9. The vascular cage of claim 6, wherein said cross-section having the varying shape, size, area, and/or longitudinal thickness profile is formed by preferential etching of said band.

10. The vascular cage of claim 1, wherein the self-expandable frame is generally spherical or ovoid in its expanded configuration.

11. The vascular cage of claim 1, wherein the self-expandable frame comprises at least one dimpled portion in its expanded configuration.

12. The vascular cage of claim 1, further comprising a wire coil wrapped around a portion of at least some of the plurality of bands.

13. The vascular cage of claim 12, wherein the wire coil comprises a substantially rectangular shaped cross-section.

14. The vascular cage of claim 13, wherein the wire coil comprises a radio opaque material.

15. The vascular cage of claim 14, wherein the radio opaque material comprises a metal selected from the group consisting of platinum and platinum alloys.

16. The vascular cage of claim 12, wherein the wire coil is configured to provide structural reinforcement to said plurality of bands.

17. The vascular cage of claim 12, wherein the wire coil is not wrapped around a distal portion of said plurality of bands in order to allow bendability or flexibility of the bands at said distal portions.

18. The occlusive system of claim 2, wherein the cage delivery catheter comprises a shaft having the lumen, a sidewall, at least one urging element formed in the sidewall, and a first filament disposed in the lumen.

19. The vascular cage of claim 1, wherein the three-dimensional cage provides an interior space allowing one or more embolic coils to be deployed therein or proximate thereto.

20. The vascular cage of claim 1, wherein the self-expandable frame comprises three to ten elongated flexible bands.

21. The vascular cage of claim 20, wherein the self-expandable frame preferentially comprises five to eight elongated flexible bands.

22. A method of occluding a vascular location, said method comprising:
   providing the vascular cage of claim 1,
   delivering the vascular cage while constrained in its compressed configuration to a target site in the vasculature,
   releasing the vascular cage from constraint so that it expands to its expanded configuration at the target location.

23. The method of claim 22, wherein delivering comprises:
   positioning a distal end of a cage delivery catheter at a target location in a patient's vasculature,
   advancing the vascular cage in its compressed configuration through a lumen of the cage delivery catheter.

24. The method of claim 22, wherein releasing comprises releasing the vascular cage from the distal end of the cage delivery catheter so that the vascular cage self-expands at the target location.

25. The method of claim 22, wherein the target location is an aneurysm.

26. The method of claim 22, wherein the target location is a blood vessel lumen.

27. The method of claim 22, further comprising delivering coils into the interior volume of the vascular cage or proximate to the vascular cage after the vascular cage has been released.

* * * * *